(12) United States Patent
Vellanki et al.

(10) Patent No.: US 10,730,888 B2
(45) Date of Patent: Aug. 4, 2020

(54) PROCESS FOR THE PREPARATION OF DOLUTEGRAVIR

(71) Applicant: Mylan Laboratories Ltd., Hyderabad (IN)

(72) Inventors: Sivaram Prasad Vellanki, Hyderabad (IN); Madumurthy Nadella, Hyderabad (IN); Mitali Bhalme, Hyderabad (IN); Revathi Srinivas Ramabhotla, Hyderabad (IN); Venkata Siva Reddy Arumalla, Hyderabad (IN); Raveendra Babu Kilaru, Hyderabad (IN)

(73) Assignee: Mylan Laboratories Limited (IN)

( * ) Notice: Subject to any disclaimer, the term of this patent is extended or adjusted under 35 U.S.C. 154(b) by 0 days.

(21) Appl. No.: 15/549,034

(22) PCT Filed: Feb. 5, 2016

(86) PCT No.: PCT/IN2016/050046
§ 371 (c)(1),
(2) Date: Aug. 4, 2017

(87) PCT Pub. No.: WO2016/125192
PCT Pub. Date: Aug. 11, 2016

(65) Prior Publication Data
US 2018/0244693 A1    Aug. 30, 2018

(30) Foreign Application Priority Data

Feb. 6, 2015 (IN) .............................. 588/CHE/2015
Aug. 7, 2015 (IN) .......................... 4137/CHE/2015

(51) Int. Cl.
C07D 498/14 (2006.01)
C07D 211/14 (2006.01)
C07C 229/30 (2006.01)
C07F 5/02 (2006.01)
C07C 227/18 (2006.01)
C07C 227/10 (2006.01)
C07D 211/02 (2006.01)
C07D 211/86 (2006.01)

(52) U.S. Cl.
CPC .......... *C07D 498/14* (2013.01); *C07C 227/10* (2013.01); *C07C 227/18* (2013.01); *C07C 229/30* (2013.01); *C07D 211/02* (2013.01); *C07D 211/86* (2013.01); *C07F 5/022* (2013.01)

(58) Field of Classification Search
CPC .. C07D 495/14; C07D 211/44; C07D 211/14; C07C 229/30
USPC ............................................... 544/73; 546/88
See application file for complete search history.

(56) References Cited

U.S. PATENT DOCUMENTS

| | | | | |
|---|---|---|---|---|
| 7,858,788 B2* | 12/2010 | Yoshida | ................ | C07F 9/6561 544/117 |
| 8,129,385 B2 | 3/2012 | Johns | | |
| 8,889,877 B2 | 11/2014 | Goodman | | |
| 9,505,783 B2* | 11/2016 | Sumino | ................ | C07D 213/80 |
| 9,758,515 B2* | 9/2017 | Takahashi | ............ | C07D 471/04 |
| 9,963,430 B2* | 5/2018 | Reddy | ................. | C07D 213/80 |

FOREIGN PATENT DOCUMENTS

WO    2011/119566 A1    9/2009

OTHER PUBLICATIONS

Abu-Shanab, Journal of Heterocyclic Chemistry, 2009, 46: 801-827, "Dimethylformamide Dimethyl Acetal as a Building Block in Heterocyclic Synthesis". Published Electronically Sep. 1, 2009.

\* cited by examiner

*Primary Examiner* — Venkataraman Balasubramanian

(57) ABSTRACT

Processes for the preparation of dolutegravir and pharmaceutically acceptable salts utilizing alkenylamine are disclosed. Intermediates in those synthetic schemes are also disclosed.

16 Claims, No Drawings

PROCESS FOR THE PREPARATION OF DOLUTEGRAVIR

CROSS-REFERENCE TO RELATED APPLICATIONS

This is a national stage entry under 35 U.S.C. § 371 of PCT Application No. PCT/IN2016/050046, with a filing date of Feb. 5, 2016, which in turn claims priority to Indian Provisional Application No. 588/CHE/2015, filed Feb. 6, 2015, and to Indian Provisional Application No. 4137/CHE/2015, filed Aug. 7, 2015, each of which are hereby incorporated by reference in their entirety.

BACKGROUND OF THE INVENTION

Field of the Invention

The present invention relates generally to the pharmaceutical arts, and more particularly to a process for the preparation of dolutegravir or pharmaceutically acceptable salts thereof.

Background of the Invention

Dolutegravir (DTG, GSK1349572) is an integrase inhibitor developed for the treatment of human immunodeficiency virus (HIV)-1 infection.

TIVICAY® tablets contain dolutegravir sodium, which is an HIV-1 integrase strand transfer inhibitor (INSTI). Dolutegravir sodium is chemically known as sodium (4R, 12aS)-9-((2,4-difluorobenzyl)carbamoyl)-4-methyl-6, 8-dioxo-3,4, 6,8,12,12a-hexahydro-2H-pyrido [1',2':4,5] pyrazino[2, 1-b] [1,3]oxazin-7-olate, having the structure below:

Formula-I

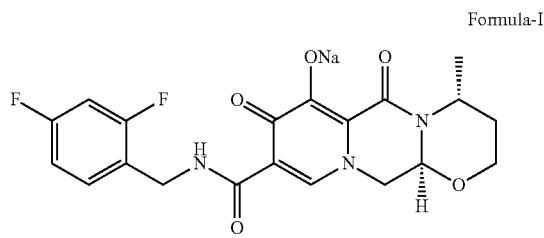

PCT Publication No. WO2006/116764A1 discloses a process for the preparation of dolutegravir.

PCT Publication No. WO2011/119566A1 also discloses a process for the preparation of dolutegravir.

The present invention provides a process for the preparation of dolutegravir and pharmaceutically acceptable salts thereof. The present invention further provides novel intermediates that may be used in processes for the preparation of dolutegravir and pharmaceutically acceptable salts thereof.

SUMMARY OF THE INVENTION

The present invention provides novel synthetic schemes for the synthesis of dolutegravir, which include the generation of novel synthetic intermediates. Together, these schemes and intermediates provide an improved, efficient method for the synthesis of dolutegravir.

In one aspect, the present invention encompasses a process for the preparation of dolutegravir, having the steps of:

a) reacting a compound of formula 8 with 1,1-dimethoxy-N,N-dimethyl methanamine to obtain a compound of formula 7;

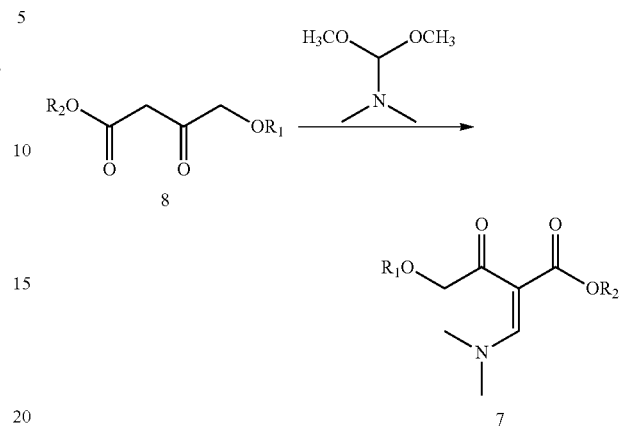

b) treating the compound of formula 7 with an alkenyl amine to obtain a compound of formula 6;

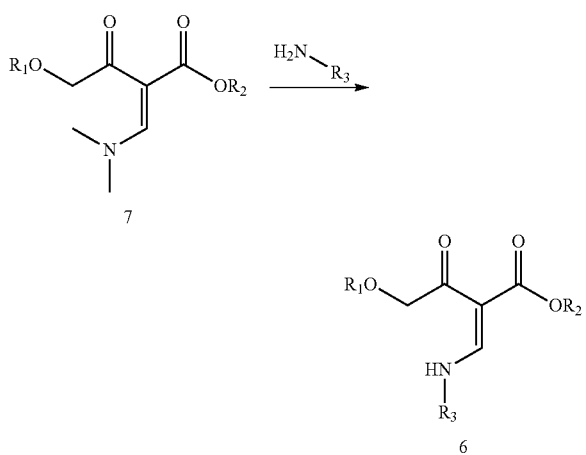

c) cyclizing the compound of formula 6 with dimethyl oxalate to obtain a compound of formula 5;

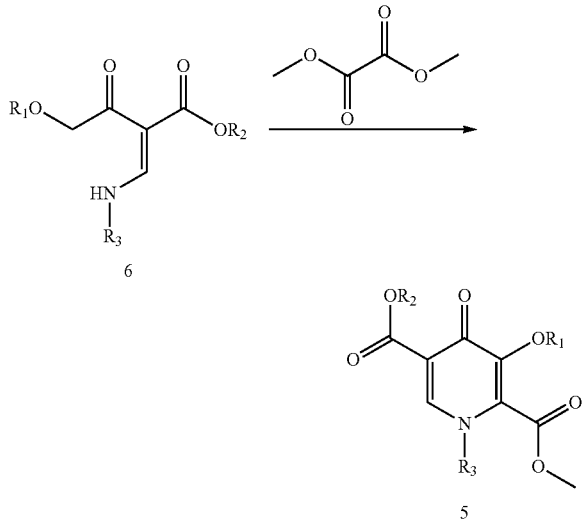

d) converting the compound of formula 5 to a compound of formula 4;

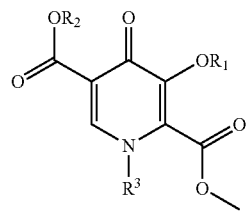

5

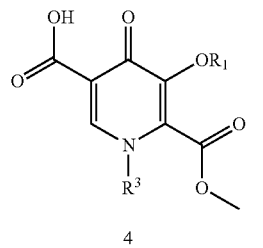

4 e) condensing the compound of formula 4 with 2,4-difluorobenzylamine to obtain a compound of formula 3;

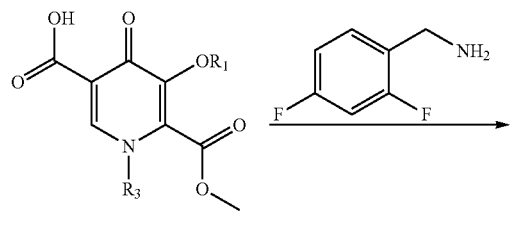

f) oxidizing the compound of formula 3 to obtain a compound of formula 2;

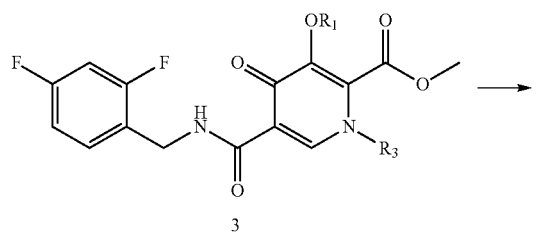

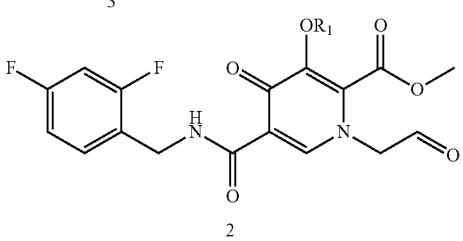

2 g) reacting the compound of formula 2 with (R)-3-aminobutanol to obtain a compound of formula 1; and

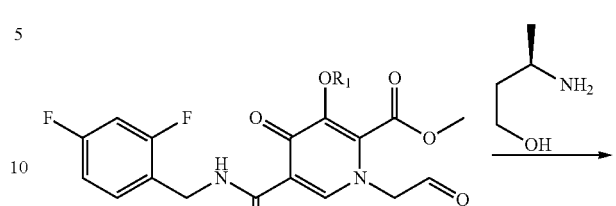

2

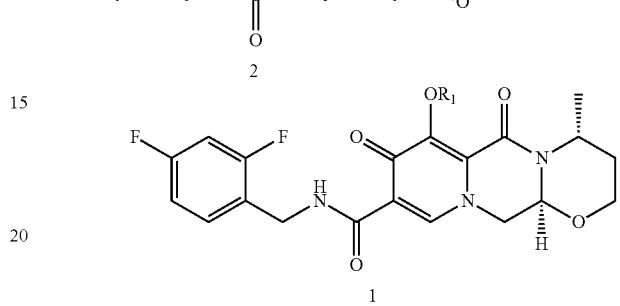

1 h) converting the compound of formula 1 to dolutegravir.

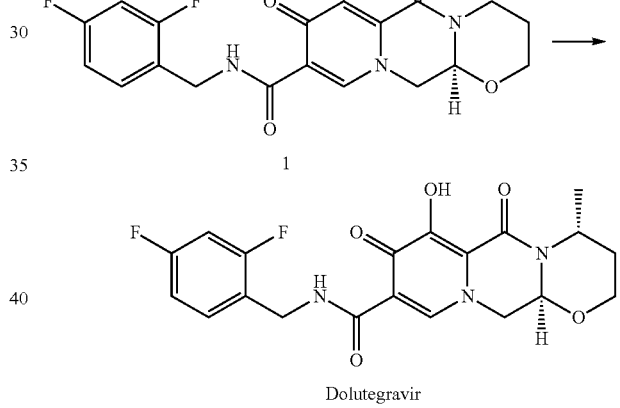

Dolutegravir wherein $R_1$ and $R_2$ are independently hydrogen, a $C_1$-$C_6$ alkyl, a $C_6$-$C_{10}$ aryl, or a $C_6$-$C_{10}$ aralkyl group and $R_3$ is a $C_2$-$C_6$ alkenyl group.

Step b) may be performed in the presence of a solvent, which may be an alcohol solvent, an ester solvent, an ether solvent, an aromatic hydrocarbon solvent, or mixtures thereof. In some embodiments, the alkenyl amine in step two may be allyl amine and the solvent may be methanol.

The cyclizing step (i.e., step c)) may be carried out in the presence of a base, which may be an alkali metal hydroxide, an alkali metal hydride, or an alkali metal alkoxide, or mixtures thereof. When used, the alkali metal hydroxide may be lithium hydroxide, sodium hydroxide, potassium hydroxide, cesium hydroxide, or mixtures thereof. When used, the alkali metal hydride may be lithium hydride, sodium hydride, potassium hydride, or mixtures thereof. When used, the alkali metal alkoxides may be lithium methoxide, sodium methoxide, sodium ethoxide, sodium tert-butoxide, potassium tert-butoxide, or mixtures thereof. In certain embodiments, the base used in this step of the disclosed method is sodium methoxide.

The converting of a compound of formula 5 to a compound of formula 4 (i.e., step d)) is carried out by converting the compound of formula 5 to a compound of formula 5a then converting the compound of formula 5a to the compound of formula 4, wherein R₁, R₂, R₃ are as defined above and X is a halogen, a $C_1$-$C_6$ alkyl, a $C_1$-$C_6$ alkoxy, a $C_1$-$C_5$ acyl, or a $C_1$-$C_5$ acyloxy group.

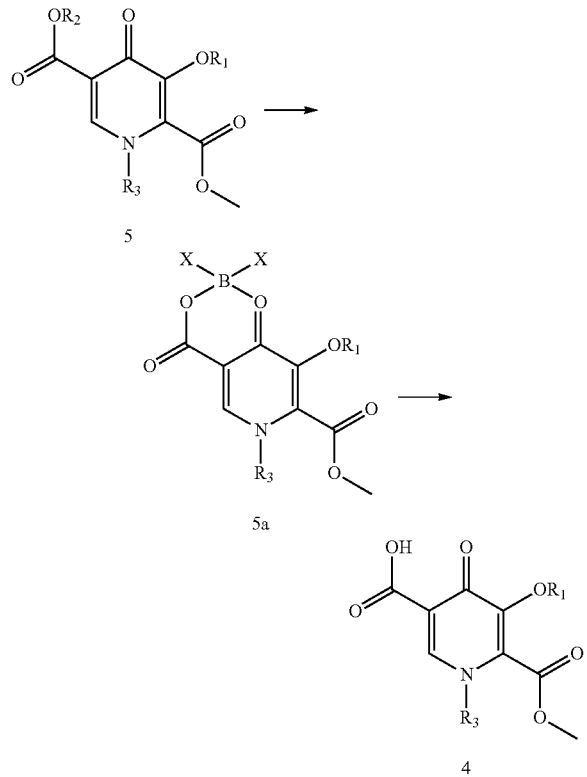

This step may be undertaken in the presence of a solvent and an acid or an alkali metal hydroxide base. The solvent used in this step may be an alcohol solvent, an ester solvent, an aromatic hydrocarbon solvent, a ketone solvent, a chlorinated hydrocarbon solvent, or mixtures thereof. The acid used in this step may be hydrochloric acid, hydrobromic acid, sulfuric acid, formic acid, acetic acid, trifluoro acetic acid, p-toluene sulfonic acid, or mixtures thereof. If an alkali metal hydroxide base is used, it may be lithium hydroxide, sodium hydroxide, potassium hydroxide, cesium hydroxide, or mixtures thereof. In certain embodiments, the solvent is methanol and the acid is hydrochloric acid in methanol.

The condensing step (i.e., step e)) may be carried out in the presence of a base, which may be N-methylmorpholine (NMM), diisopropylethylamine, triethylamine, N,N'-dimethylpiperazine, N-methylpiperidine, pyridine, or mixtures thereof. In certain embodiments, the base used in this step is N-methylmorpholine. The condensing step may also be carried out in the presence of a coupling agent, which may be isobutyl chloroformate, carbonyldiimidazole (CDI), pivaloyl chloride, o-benzotriazole-1-yl-1,1,3,3-tetramethyluronium tetrafluoroborate (TBTU), 2-(1H-benzotriazole-1-yl)-1,1,3,3-tetramethyluronium (HBTU), benzotriazole-1-yl-oxy-tris(dimethylamino)phosphonium (BOP), benzotriazole-1-yl-oxy-tris(pyrrolidino) phosphonum (Py-BOP), bromo-tris-pyrrolidino-phosphoniumhexaflurophosphate (PyBrOP), tris(pyroolidino)phosphonium hexafluorophosphate (pyCOP), ethyl cyanoglyoxylate-2-oxime, o-(6-chloro-1-hydroxybenzotriazol-1-yl)-1,1,3,3-tetramethyluronium tetrafluoroborate (TCTU), 2-(1H-7-azabenzotriazol-1-yl)-1,1,3,3-tetramethyl uronium hexafluorophosphate (HATU), 1-cyano-2-ethoxy-2-oxoethydenminooxy)dimethylamino-morpholion-carbenium hexafluorophosphate (COMU), or mixtures thereof. In certain embodiments, the coupling agent used in this step is isobutyl chloroformate.

The condensing step may also be carried out in the presence of an additive such as, for example, hydroxyl benzotriazole (HOBt), 1-hydroxy-7-azabenzotriazole (HOAt), 6-chloro-1-hydroxy-1H-benzotriazole (Cl-HOBt), hydroxypyridines (HOPy), imidazole or its salts, 1,8-diazabicyclo[5.4.0]undec-7-en (DBU), dimethylaminopyridine (DMAP), or mixtures thereof.

The oxidizing step in this method (i.e., step f)) may be carried out using an oxidizing agent, such as, for example, ozone, ozonized oxygen, periodic acid, osmium tetroxide-periodate, ruthenium trichloride-periodate, sodium metaperiodate, sodium orthoperiodate, ruthenium trichloride/potassium peroxymonosulfate, bis(acetonitrile)dichloropalladium (II), bis(benzonitrile)palladium(II)chloride, or mixtures thereof. In certain embodiments, the oxidizing agent used in this step is ozone or ozonized oxygen.

The step where the compound of formula 2 is reacted with (R)-3-aminobutanol to obtain a compound of formula 1 (i.e., step g)) may be conducted in the presence of a solvent and an acid. The solvent may be an alcohol solvent, an aromatic hydrocarbon solvent, an ether solvent, an ester solvent, a polar aprotic solvent, or mixtures thereof. The acid used in this step may be acetic acid, methane sulfonic acid, p-toluenesulfonic acid, or mixtures thereof. In certain embodiments, the solvent used in this step is acetonitrile and the acid is acetic acid.

This process may also include the step of converting dolutegravir to a pharmaceutically acceptable salt of dolutegravir.

In another aspect, present invention provides a process for the preparation of dolutegravir that includes the steps of:
a) cyclizing a compound of formula 14 with dimethyl oxalate to obtain a compound of formula 13;

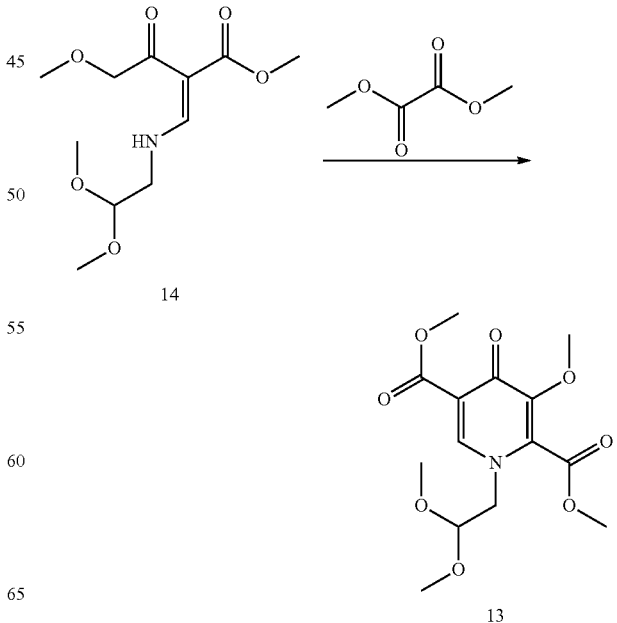

b) treating the compound of formula 13 with boric acid to obtain a compound of formula 12;

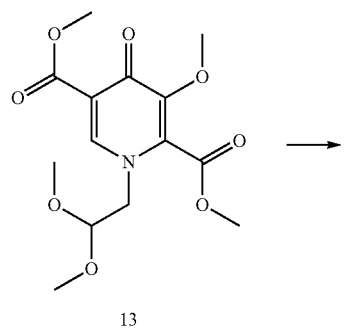

13

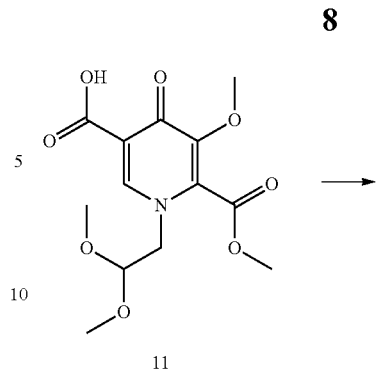

11

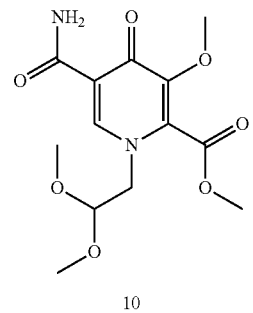

10 e) reacting the compound of formula 10 with (R)-3-aminobutanol to obtain a compound of formula 9;

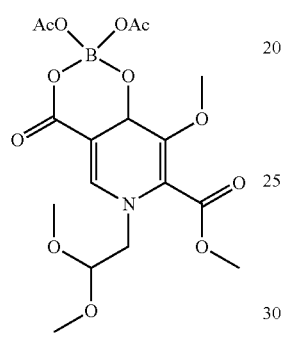

12 c) reacting the compound of formula 12 with an acid to obtain a compound of formula 11;

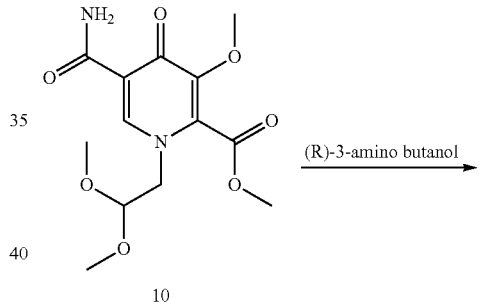

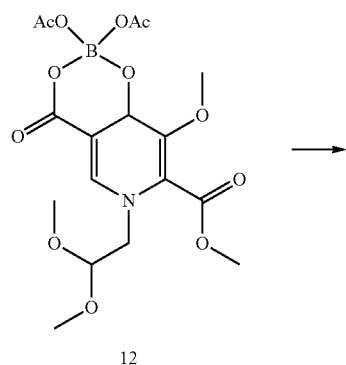

12

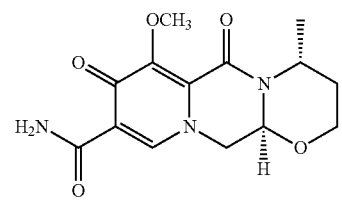

9 f) condensing the compound of formula 9 with 2,4-diflurobenzaldehyde to obtain a compound of formula 1a; and

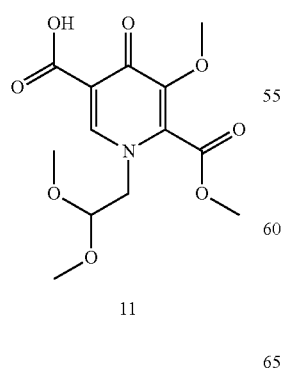

11

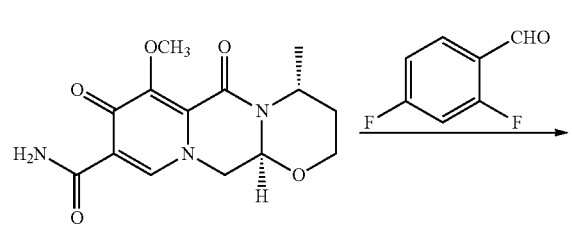

9 d) converting the compound of formula 11 to a compound of formula 10;

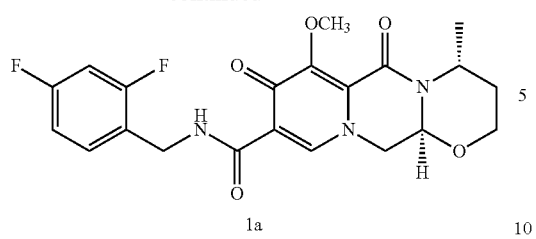

1a g) converting the compound of formula 1a to dolutegravir.

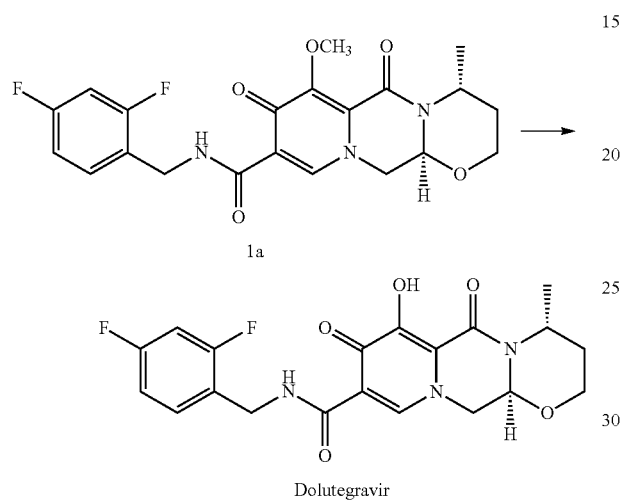

1a

Dolutegravir

The cyclizing step (i.e., step a)) of this method may be carried out in presence of a base and a solvent. In certain embodiments, the base is sodium hydride and solvent is selected from the group consisting of tetrahydrofuran, 1,2-dimethoxyethane, and mixtures thereof.

This process may also include the step of converting dolutegravir to a pharmaceutically acceptable salt of dolutegravir.

Yet another of aspect of the present invention provides a process for the preparation of dolutegravir, which is as shown in scheme-I:

Scheme-I

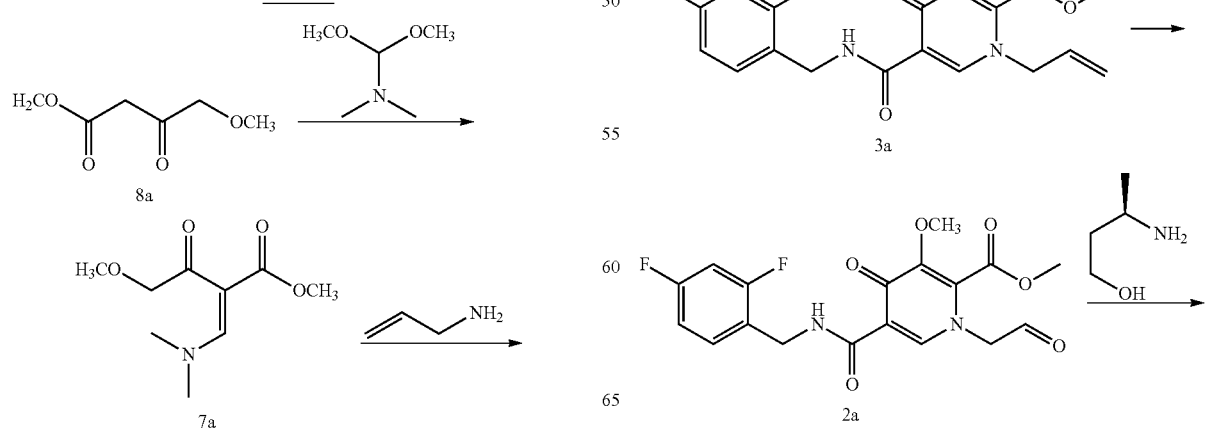

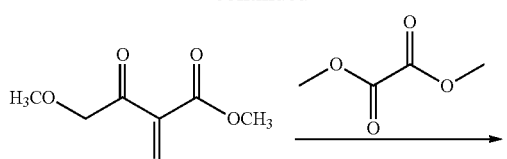

6a

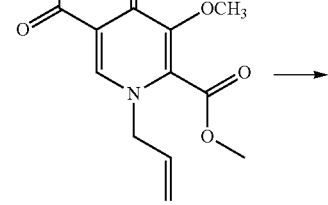

5b

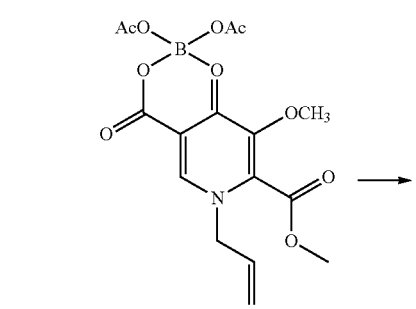

5c

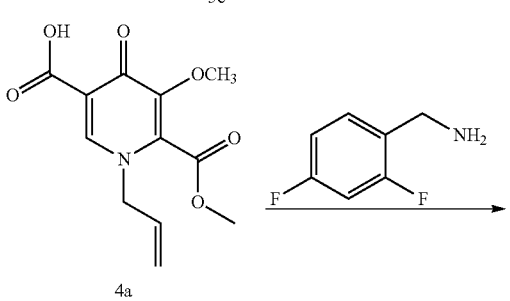

4a

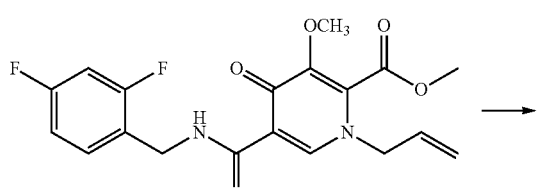

3a

2a

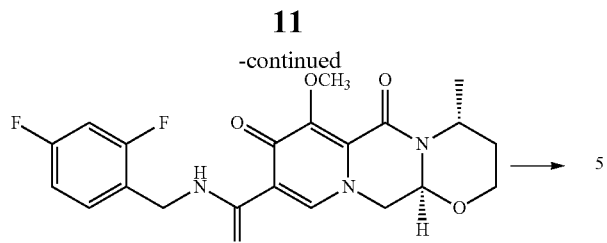

1a

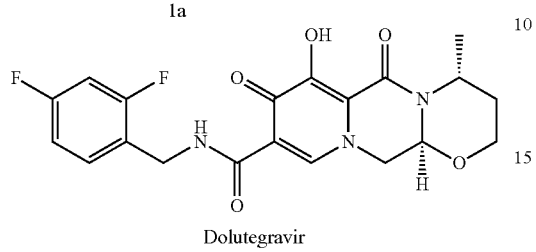

Dolutegravir

DETAILED DESCRIPTION OF THE DISCLOSURE

It is to be understood that the descriptions of the present invention have been simplified to illustrate elements that are relevant for a clear understanding of the invention.

The present invention provides novel synthetic schemes for the synthesis of dolutegravir. Within the context of the present invention, novel intermediates are generated as part of the novel synthetic schemes. Together, these schemes and intermediates provide an improved, efficient method for the synthesis of dolutegravir.

One embodiment of the present invention provides a process for the preparation of dolutegravir or pharmaceutically acceptable salts thereof.

According to an embodiment of the present invention, dolutegravir may be prepared by the following steps:

a) reacting a compound of formula 8 with 1,1-dimethoxy-N,N-dimethyl methanamine (DMF-DMA) to obtain a compound of formula 7;

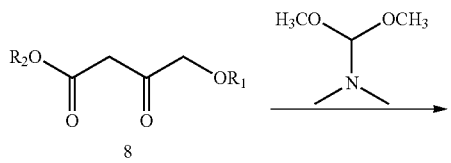

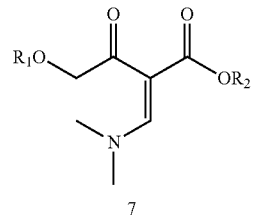

7 b) treating the compound of formula 7 with alkenyl amine to obtain a compound of formula 6; and

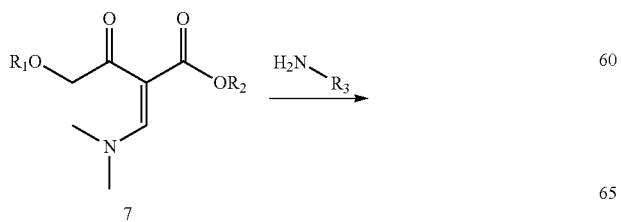

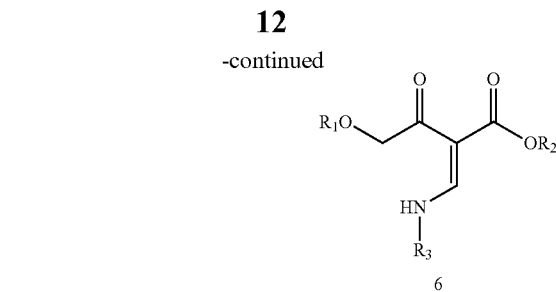

6 c) cyclizing the compound of formula 6 with dimethyl oxalate to obtain a compound of formula 5.

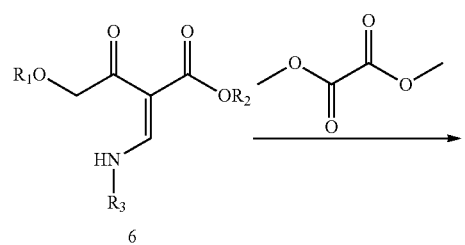

6

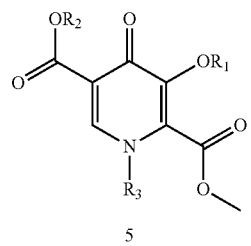

5

Within the context of the present invention, $R_1$ and $R_2$ are independently hydrogen, $C_1$-$C_6$ alkyl, $C_6$-$C_{10}$ aryl, or $C_6$-$C_{10}$ aralkyl group, and $R_3$ is a $C_2$-$C_6$ alkenyl group.

Within the context of this embodiment of the present invention, a compound of formula 5 may then be converted to a compound of formula 4 directly ("direct conversion") or by first converting a compound of formula 5 to a boron complex of formula 5a, which is then converted to a compound of formula 4 ("indirect conversion"), as shown in the two synthetic schemes below.

Direct Conversion

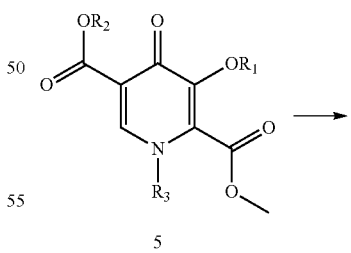

5

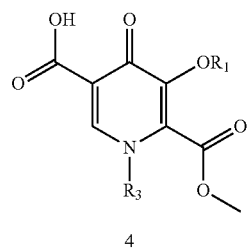

4

Indirect Conversion

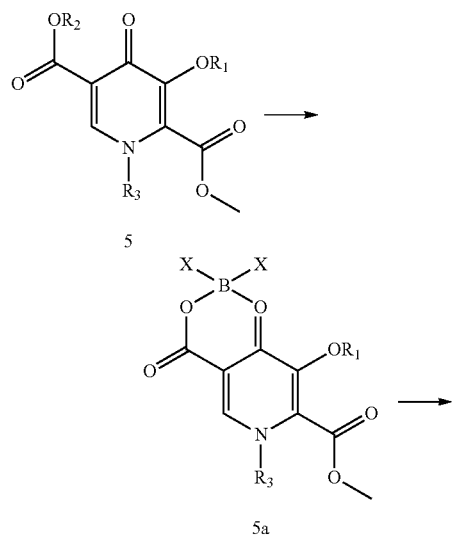

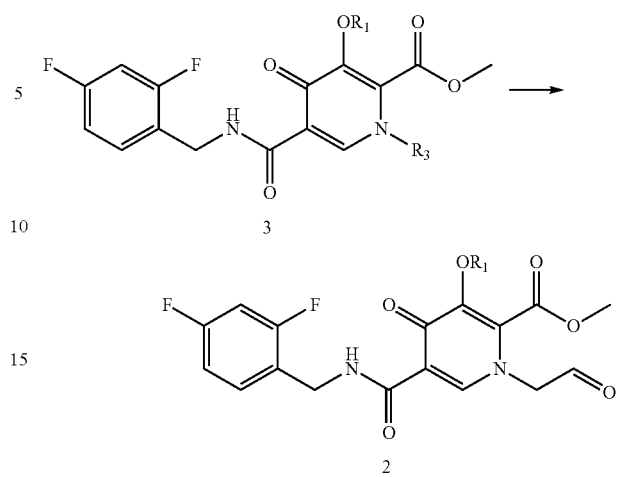

Within the context of the present invention, $R_1$, $R_2$, and $R_3$ are defined as above; X is a halogen, a $C_1$-$C_6$ alkyl, a $C_1$-$C_6$ alkoxy, a $C_1$-$C_5$ acyl, or a $C_1$-$C_5$ acyloxy group.

Within the context of the present invention, a compound of formula 4 may then be converted to dolutegravir or a pharmaceutically acceptable salt thereof by the following steps:

1. condensing a compound of formula 4 with 2,4-difluorobenzylamine to obtain a compound of formula 3;

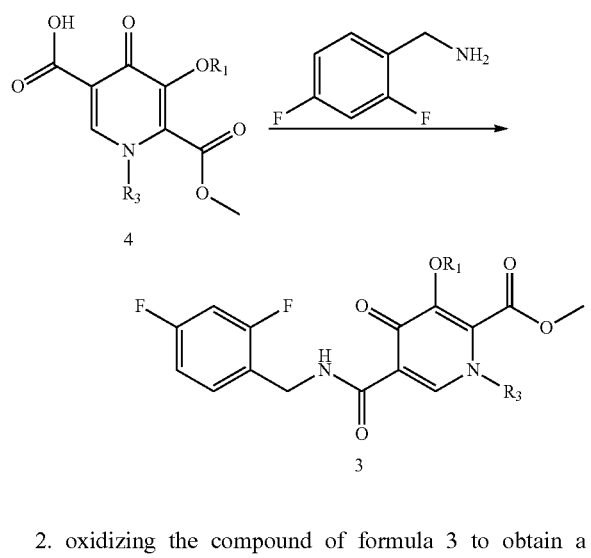

2. oxidizing the compound of formula 3 to obtain a compound of formula 2;

3. reacting the compound of formula 2 with (R)-3-aminobutanol to obtain a compound of formula 1; and

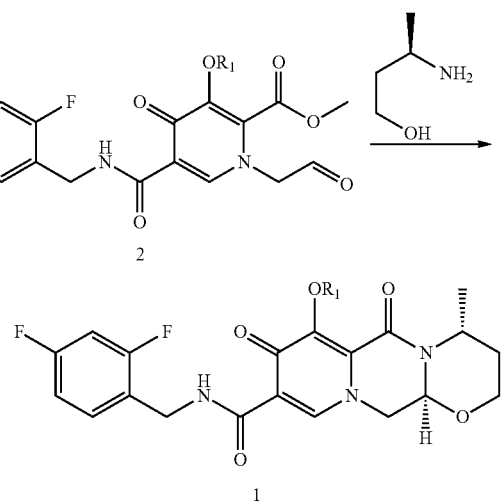

4. converting the compound of formula 1 to dolutegravir.

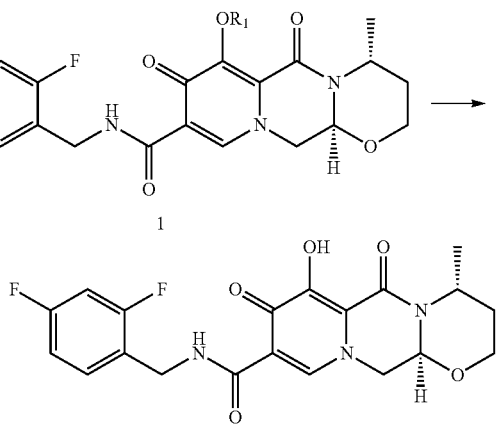

Within the context of the present invention, $R_1$ and $R_2$ are independently hydrogen, a $C_1$-$C_6$ alkyl, a $C_6$-$C_{10}$ aryl, or $C_6$-$C_{10}$ aralkyl group and $R_3$ is $C_2$-$C_6$ alkenyl group.

According to this embodiment of the present invention, a compound of formula 8 may be reacted with 1,1-dimethoxy-N,N-dimethyl methanamine (DMF-DMA) to obtain a compound of formula 7. In particularly useful embodiments of the present invention, $R_1$ and $R_2$ in formula 8 are methyl groups.

According to this embodiment of the present invention, a compound of formula 7 may then be treated with an alkenyl amine to yield a compound of formula 6. This reaction may be carried out in a solvent, for example, an alcohol such as methanol or ethanol, an ester such as ethyl acetate or isopropyl acetate, an ether such as tetrahydrofuran, an aromatic hydrocarbon such as toluene, or mixtures thereof. In particularly useful embodiments of the present invention, the alkenyl amine is allylamine and methanol is used as a solvent.

According to this embodiment of the present invention, a compound of formula 6 may then be cyclized with dimethyl oxalate to obtain a compound of formula 5. This reaction may be carried out in the presence of base and a solvent.

Within the context of this embodiment of the present invention, the base may be, for example, an alkali metal hydroxide, an alkali metal hydride, or an alkali metal alkoxides, and mixtures thereof. Examples of suitable alkali metal hydroxides include lithium hydroxide, sodium hydroxide, potassium hydroxide, cesium hydroxide, and mixtures thereof. Examples of suitable alkali metal hydrides include lithium hydride, sodium hydride, potassium hydride, and mixtures thereof. Examples of suitable alkali metal alkoxides include lithium methoxide, sodium methoxide, sodium ethoxide, sodium tert-butoxide, potassium tert-butoxide, and mixtures thereof. In particularly useful embodiments of the present invention, sodium methoxide is used as a base. One of skill in the art will recognize numerous other bases that may be useful within the context of the present invention for carrying out the cyclization of a compound of formula 6 with dimethyl oxalate to obtain a compound of formula 5.

Within the context of the present invention, examples of suitable solvents include alcohols such as methanol, ethanol, isopropanol, and mixtures thereof. In particularly useful embodiments of the present invention, methanol is used as a solvent.

According to this embodiment of the present invention, a compound of formula 5 may then be converted to a compound of formula 4. This may occur by direct conversion of a compound of formula 5 to a compound of formula 4 or by indirect conversion of a compound of formula 5 to a compound of formula 5a which is then converted to a compound of formula 4.

Direct conversion of a compound of formula 5 to a compound of formula 4 may occur by hydrolysis of a compound of formula 5 in the presence of a base or an acid in a suitable solvent.

Within the context of this embodiment of the present invention, suitable solvents include alcohols such as methanol, ethanol, isopropanol, and mixtures thereof. In particularly useful embodiments of the present invention, methanol is used as a solvent.

Within the context of this embodiment of the present invention, examples of suitable acids include hydrochloric acid, hydrobromic acid, sulfuric acid, formic acid, acetic acid, p-toluenesulfonic acid, and mixtures thereof. One of skill in the art will recognize numerous other acids that may be useful to convert a compound of formula 5 to a compound of formula 4.

Within the context of this embodiment of the present invention, examples of suitable bases include alkali metal hydroxides. Suitable alkali metal hydroxides include, as examples, lithium hydroxide, sodium hydroxide, potassium hydroxide, cesium hydroxide, and mixtures thereof. In particularly useful embodiments of the present invention, lithium hydroxide is used as a base. One of skill in the art will recognize numerous other bases that may be useful to convert formula compound of 5a to a compound of formula 4.

Indirect conversion of a compound of formula 5 to a compound of formula 4 may first occur by converting the compound of formula 5 to a compound of formula 5a. In some embodiments of the present invention, boric acid is first mixed with acetic acid which is then reacted with a compound of formula 5 to result in a compound of formula 5a.

A compound of formula 5a may then be converted to a compound of formula 4 in the presence of a base or an acid and a suitable solvent.

Within the context of this embodiment of the present invention, examples of suitable acids include hydrochloric acid, hydrobromic acid, sulfuric acid, formic acid, acetic acid, trifluoro acetic acid, p-toluene sulfonic acid, and mixtures thereof. In particularly useful embodiments of the invention, hydrochloric acid in methanol (methanolic HCl) is used as an acid. One of skill in the art will recognize numerous acids that may be useful to remove the boron complex on a compound of formula 5a to obtain a compound of formula 4.

Within the context of this embodiment of the present invention, examples of suitable bases include alkali metal hydroxides. Suitable alkali metal hydroxides include, as examples, lithium hydroxide, sodium hydroxide, potassium hydroxide, cesium hydroxide, and mixtures thereof. One of skill in the art will recognize numerous bases that may be useful to remove the boron complex on a compound of formula 5a to obtain a compound of formula 4.

Within the context of this embodiment of the present invention, examples of suitable solvents include alcohols such as methanol or ethanol, esters such as ethyl acetate, ethers such as tetrahydrofuran, aromatic hydrocarbons such as toluene, ketones such as methyl isobutyl ketone, chlorinated hydrocarbons such as methylene dichloride, and mixtures thereof. In particularly useful embodiments of the present invention, methanol is used as a solvent.

According to this embodiment of the present invention, a compound of formula 4 may then be condensed with 2,4-difluorobenzylamine to obtain a compound of formula 3. This reaction may occur in presence of a base and a coupling agent in a suitable solvent. Optionally, an additive may be also be used in this reaction. Within the context of this embodiment of the invention, the additive may enhance the reaction, for example, to increase the rate of the reaction or to control the product distribution.

Within the context of this embodiment of the present invention, the base may be, for example, N-methylmorpholine (NMM), N,N-diisopropylethylamine, triethylamine, N,N'-dimethylpiperazine, N-methylpiperidine, pyridine, or mixtures thereof. In particularly useful embodiments of the present invention, N-methylmorpholine is used as a base. One of skill in the art will recognize numerous bases that may be useful for this reaction.

Within the context of this embodiment of the present invention, the coupling agent may be, for example, isobutyl chloroformate, carbonyldiimidazole (CDI), pivaloyl chloride, o-benzotriazole-1-yl-1,1,3,3-tetramethyluronium tetrafluoroborate (TBTU), 2-(1H-benzotriazole-1-yl)-1,1,3,3-tetramethyluronium (HBTU), benzotriazole-1-yl-oxy-tris (dimethylamino)phosphonium (BOP), benzotriazole-1-yl-oxy-tris(pyrrolidino) phosphonum (PyBOP), bromo-tris-pyrrolidino-phosphoniumhexaflurophosphate (PyBrOP), tris(pyroolidino)phosphonium hexaflurophosphate (pyCOP), ethyl cyanoglyoxylate-2-oxime, o-(6-chloro-1-hydroxybenzotriazol-1-yl)-1,1,3,3-tetramethyluronium tetrafluoroborate (TCTU), 2-(1H-7-azabenzotriazol-1-yl)-1,1,3,3-tetramethyl uronium hexafluorophosphate (HATU), 1-cyano-2-ethoxy-2-oxoethydenminooxy)dimethylamino-morpholion-carbenium hexafluorophosphate (COMU), or mixtures thereof. In particularly useful embodiments of the present invention, isobutyl chloroformate is used as a coupling agent. One of skill in the art will recognize numerous additional coupling agents that may be useful for this reaction.

Within the context of this embodiment of the present invention, examples of suitable solvents include esters such as ethyl acetate, ethers such as tetrahydrofuran, chlorinated hydrocarbons such as methylene dichloride, and mixtures thereof. In particularly useful embodiments of the present invention, methylene dichloride is used as a solvent.

Within the context of this embodiment of the present invention, the additive may be, for example, hydroxyl benzotriazole (HOBt), 1-hydroxy-7-azabenzotriazole (HOAt), 6-chloro-1-hydroxy-1H-benzotriazole (Cl-HOBt), hydroxypyridines (HOPy), imidazole or its salts, 1,8-diazabicyclo [5.4.0]undec-7-en (DBU), dimethylaminopyridine (DMAP), or mixtures thereof. Within the context of the present invention, the additive may be utilized to enhance the reaction, for example, to increase the rate of the reaction, or to control the product distribution.

One of skill in the art will recognize numerous other additives that may be useful within the context of the present invention.

According to this embodiment of the present invention, a compound of formula 3 may then be oxidized to get a compound of formula 2. Within the context of the present invention, this reaction may be performed by reacting the compound of formula 3 with an oxidizing agent in the presence of a solvent. The oxidizing agent may be, for example, ozone, ozonized oxygen, periodic acid, osmium tetroxide-periodate, ruthenium trichloride-periodate, sodium metaperiodate, sodium orthoperiodate, rutheniumtrichloride/potassiumperoxymonosulfate, bis(acetonitrile)dichloropalladium(II), bis(benzonitrile)palladium(II)chloride, or mixtures thereof. In particularly useful embodiments of the present invention, a mixture of osmium tetroxide and sodium metaperiodate is used as an oxidizing agent. In other particularly useful embodiments of the present invention, the oxidizing agent is rutheniumtrichloride/potassiumperoxymonosulfate. In yet other particularly useful embodiments of the present invention, ozone gas or ozonized oxygen is used as an oxidizing agent. One of skill in the art will recognize numerous additional oxidizing agents that may be useful for oxidizing compound of formula 3 to result in a compound of formula 2.

Within the context of this embodiment of the present invention, examples of suitable solvents include alcohols such as methanol or ethanol, ethers such as tetrahydrofuran, ketones such as acetone or methyl isobutyl ketone, other polar aprotic solvents such as acetonitrile, and mixtures thereof. In particularly useful embodiments of the present invention tetrahydrofuran is used as a solvent.

A compound of formula 2 may then be reacted with (R)-3-amninobutanol to obtain a compound of formula 1. This reaction may be performed in a suitable solvent and an acid.

Within the context of this embodiment of the present invention, examples of suitable solvents include alcohols such as methanol or ethanol, aromatic hydrocarbons such as toluene, ethers such as tetrahydrofuran, esters such as ethyl acetate, polar aprotic solvents such as acetonitrile, and mixtures thereof. In particularly useful embodiments of the present invention, acetonitrile is used as a solvent.

Within the context of this embodiment of the present invention, examples of suitable acids include acetic acid, methane sulfonic acid, p-toluenesulfonic acid, and mixtures thereof. In particularly useful embodiments of the present invention, acetic acid is used. One of skill in the art will recognize numerous other acids that may be useful to convert formula 2 to formula 1.

A compound of formula 1 may then be converted to dolutegravir. This reaction may be performed in the presence of a suitable reagent and a solvent.

Examples of suitable reagents include metal bromides, for example, magnesium bromide or lithium bromide.

Examples of suitable solvents include acetonitrile, N-methyl pyrrolidone, dimethyl formamide, and mixtures thereof. In particularly useful embodiments of the present invention, magnesium bromide is used as a reagent and acetonitrile is used as solvent.

Within the context of the present invention, dolutegravir may be optionally converted into a pharmaceutically acceptable salt of dolutegravir.

The term "pharmaceutically acceptable salt" is well known and understood in the art and refers to salts of pharmaceutically active agents which are suitable for use in contact with the tissues of humans and lower animals without undue adverse effects (e.g., toxicity, irritation, allergic response). Examples of pharmaceutically acceptable salts may be found in S. M. Berge, et al., J. Pharmaceutical Sciences, 66: 1-19 (1977), in which all information pertaining to the pharmaceutically acceptable salts and processes for preparation thereof are hereby incorporated by reference.

Preparation of a pharmaceutically acceptable salt of an active pharmaceutical agent is well known in the art. For example, the salts can be prepared in situ during the final isolation and purification of the compounds taught herein or separately by reacting a free base or free acid moiety on the active pharmaceutical agent with a suitable reagent. For example, a free base moiety on dolutegravir can be reacted with a suitable acid to obtain a pharmaceutically acceptable basic salt of dolutegravir. In another example, a free acid moiety on dolutegravir may be reacted with a suitable base to obtain a pharmaceutically acceptable acid salt of dolutegravir.

Pharmaceutically acceptable salts of dolutegravir include, as basic salts, for example, alkali metal salts such as sodium or potassium salts; alkaline-earth metal salts such as calcium or magnesium salts; ammonium salts; aliphatic amine salts such as trimethylamine, triethylamine, dicyclohexylamine, ethanolamine, diethanolamine, triethanolamine or procaine salts; aralkyl amine salts such as N,N-dibenzylethylenediamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts, and basic amino acid salts such as arginine salts or lysine salts. Acid salts include, for example, mineral acid salts such as hydrochloride, sulfates salts, nitrate salts, phosphates salts, carbonates salts, hydrogencarbonates or perchlorate; organic acid salts such as acetates, propionates, lactates, maleates, fumarates, tararic acid salts, malates, citrates salts, ascorbates, formic acid; sulfonates such as methanesulfonates, isethionates, benzenesulfonates, or p-toluenesulfonates; and acidic amino acid salts such as aspartates or glutamates. In some embodiments, the sodium salt of dolutegravir is particularly useful.

Another embodiment of the present invention provides a process for the preparation of dolutegravir or a pharmaceutically acceptable salt thereof, which may include the following steps:

a) cyclizing the compound of formula 14 with dimethyl oxalate to obtain a compound of formula 13;

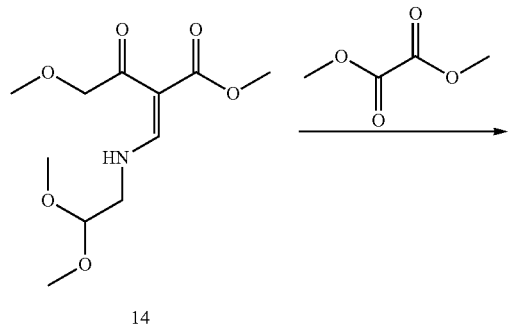

14

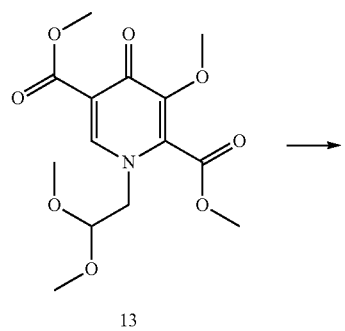

13 b) treating the compound of formula 13 with boric acid to a compound of formula 12;

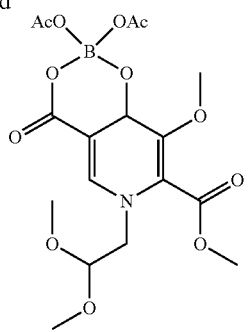

12 c) reacting the compound of formula 12 with an acid to obtain a compound of formula 11;

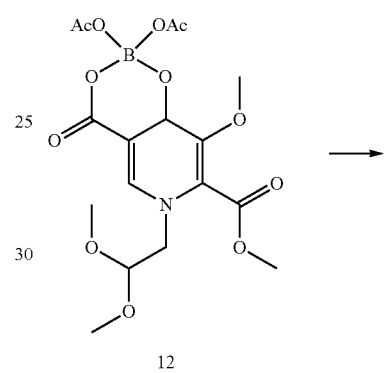

12

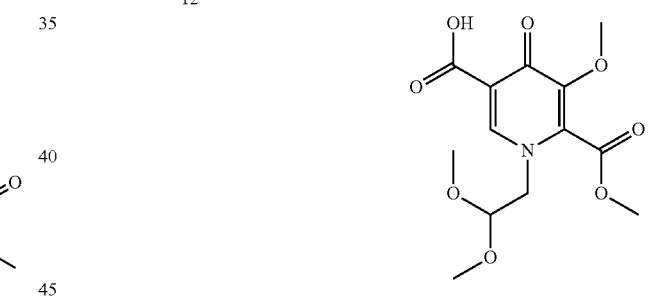

11 d) converting the compound of formula 11 to a compound of formula 10;

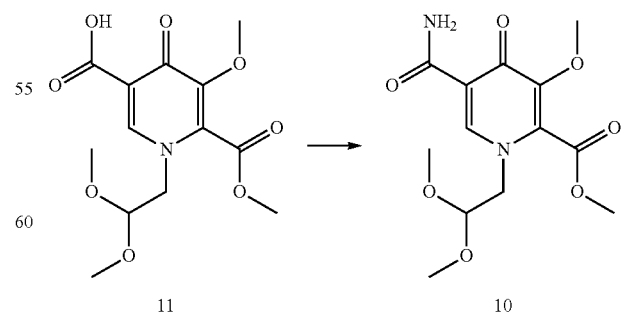

11        10 e) reacting the compound of formula 10 with (R)-3-aminobutanol to obtain a compound of formula 9;

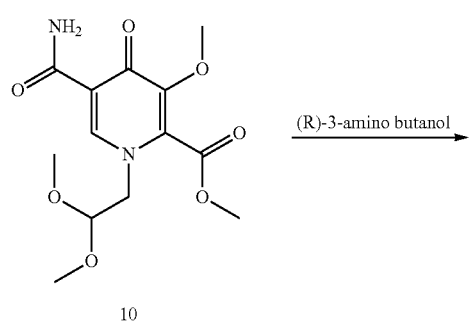

10

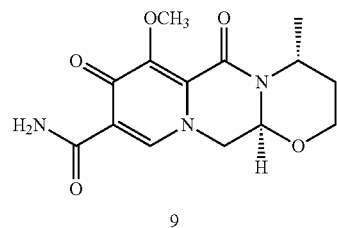

9 f) condensing the compound of formula 9 with 2,4-diflurobenzaldehyde to obtain a compound of formula 1a; and

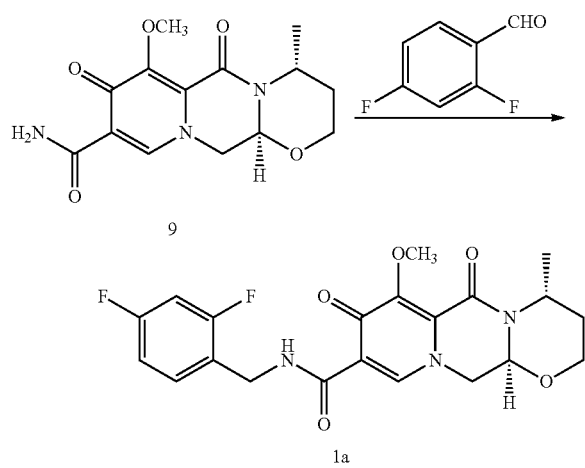

g) converting the compound of formula 1a to dolutegravir or a pharmaceutically acceptable salt thereof.

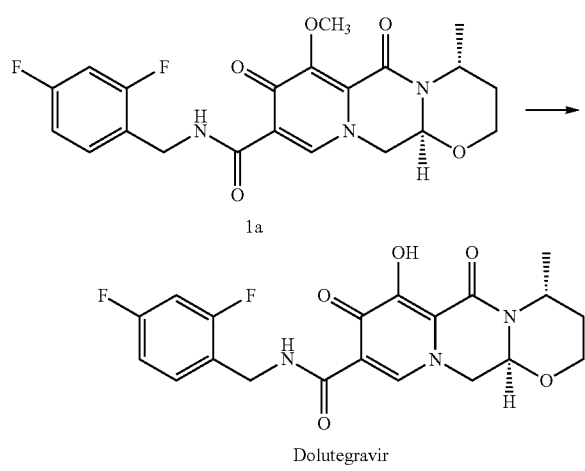

Within the context of this embodiment of the presentation, a compound of formula 14 may be prepared by the processes described previously above which includes the steps of conversion of a compound of formula 8 to a compound of formula 7 followed by the conversion of the compound of formula 7 to a compound of formula 6.

According to this embodiment of the present invention, a compound of formula 14 may be cyclized with dimethyl oxalate to obtain a compound of formula 13. This reaction may be carried out in the presence of a base, for example, sodium hydride, and a solvent, for example, tetrahydrofuran, 1,2-dimethoxyethane, or a mixture thereof.

According to this embodiment of the present invention, a compound of formula 13 may then be treated with boric acid in the presence of acetic anhydride and a suitable to yield a compound of formula 12. Examples of suitable solvents include aromatic hydrocarbons such as toluene, alcohols such as methanol, esters such as ethyl acetate, and mixtures thereof.

According to this embodiment of the present invention, a compound of formula 12 may then be treated with an acid in a suitable solvent to obtain a compound of formula 11.

Within the context of this embodiment of the present invention, examples of suitable acids include hydrochloric acid, hydrobromic acid, sulfuric acid, formic acid, acetic acid, p-toluenesulfonic acid, and mixtures thereof. In particularly useful embodiments of the invention, aqueous hydrochloric acid is used as an acid.

Within the context of this embodiment of the present invention, suitable solvents include methanol, acetone, methylene dichloride, acetonitrile, tetrahydrofuran, and mixtures thereof.

According to this embodiment of the present invention, a compound of formula 11 may then be converted to a compound of formula 10. This reaction may be carried out in the presence of ammonium chloride, 1-(3-dimethylaminopropyl)-3-ethylcarbodiimide HCl, and hydroxyl benzotriazole monohydrate in the presence of a suitable solvent. Examples of suitable solvents include tetrahydrofuran, acetone, acetonitrile, and mixtures thereof.

According to this embodiment of the present invention, a compound of formula 10 may then be treated with (R)-3-aminobutanol in presence of methane sulfonic acid and acetic acid to obtain a compound of formula 9. This reaction may be carried out in a suitable solvent, for example, acetonitrile, methylene dichloride, tetrahydrofuran, ethyl acetate, acetone, or mixtures thereof.

According to this embodiment of the present invention, a compound of formula 9 may then be reacted with 2,4-difluorobenzaldehyde to yield a compound of formula 1a. This reaction may be carried out in the presence of a reagent and a solvent.

In some embodiments of the present invention, this reagent used for this step is a mixture of triethylsilane and trifluoroacetic acid.

The solvent may be, for example, toluene, methylene dichloride, acetone, ethyl acetate, acetonitrile, and mixtures thereof. In some particularly useful embodiments of the present invention, toluene is used as a solvent.

According to this embodiment of the present invention, a compound of formula 1a may then be converted to dolutegravir. This reaction may be performed in the presence of a suitable reagent and a solvent.

Examples of suitable reagents for this step include metal bromides, for example, magnesium bromide or lithium bromide.

Examples of suitable solvents for this step include acetonitrile, N-methyl pyrrolidone, dimethyl formamide, and mixtures thereof. In particularly useful embodiments of the present invention, magnesium bromide is used as a reagent and acetonitrile is used as solvent.

Within the context of this embodiment of the present invention, dolutegravir may be optionally converted into a pharmaceutically acceptable salt of dolutegravir, as described above.

Another embodiment of the present invention provides a process for the preparation of dolutegravir or a pharmaceutically acceptable salt thereof, which is shown below in scheme-II.

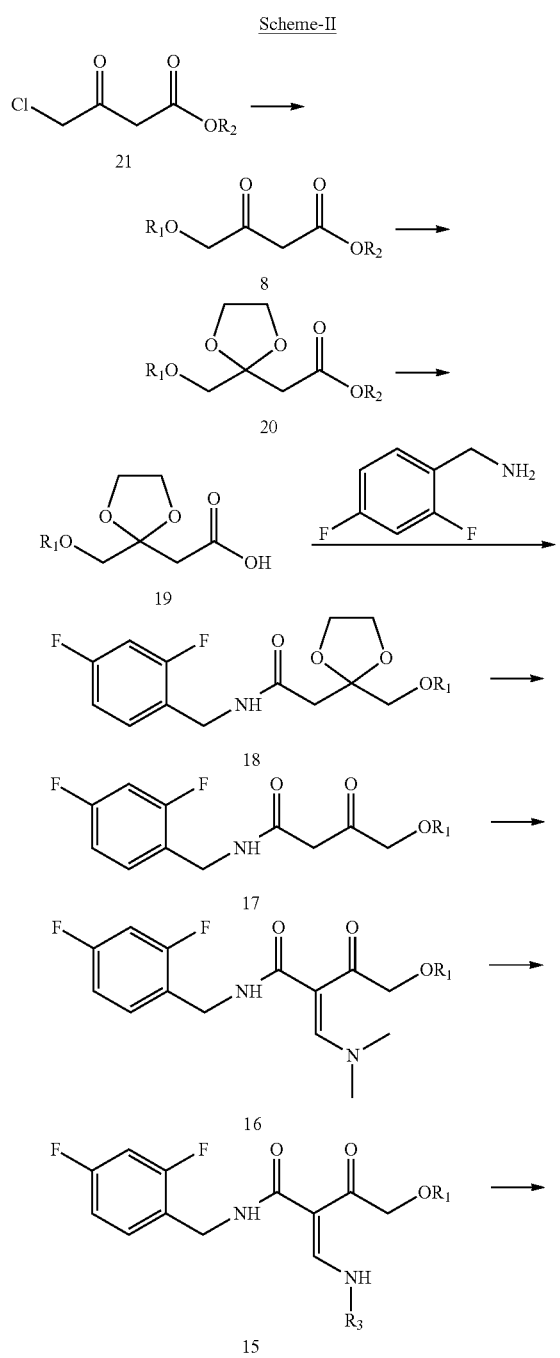

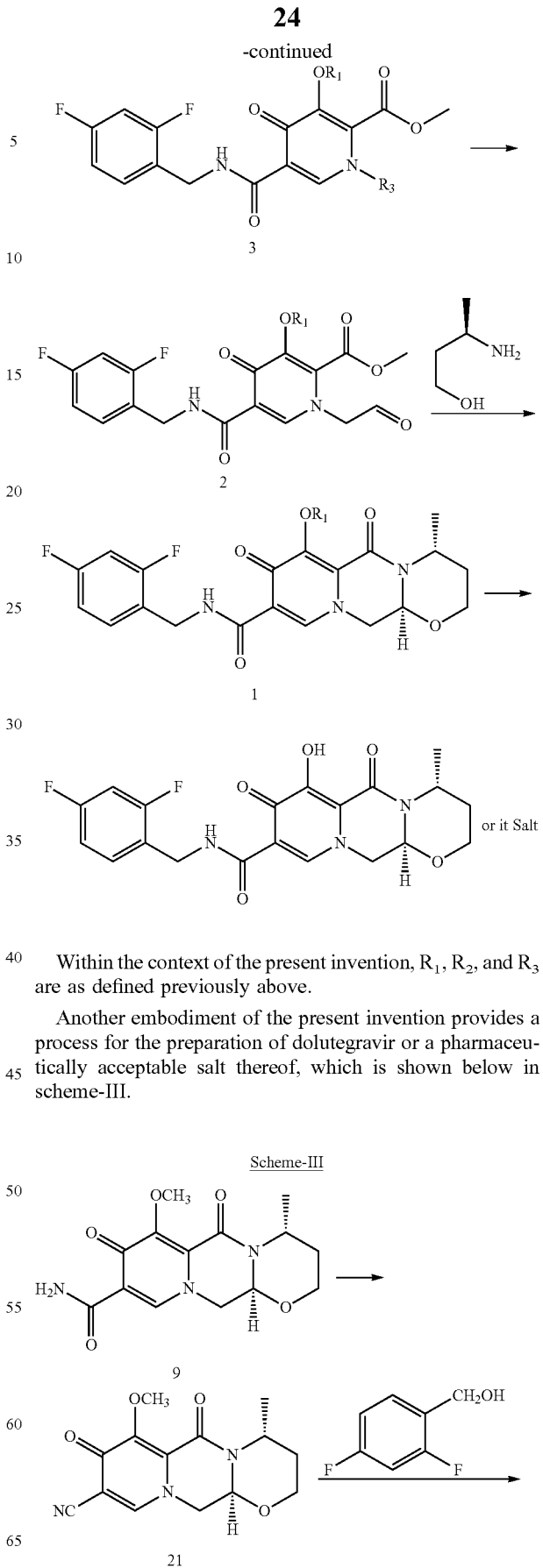

Within the context of the present invention, $R_1$, $R_2$, and $R_3$ are as defined previously above.

Another embodiment of the present invention provides a process for the preparation of dolutegravir or a pharmaceutically acceptable salt thereof, which is shown below in scheme-III.

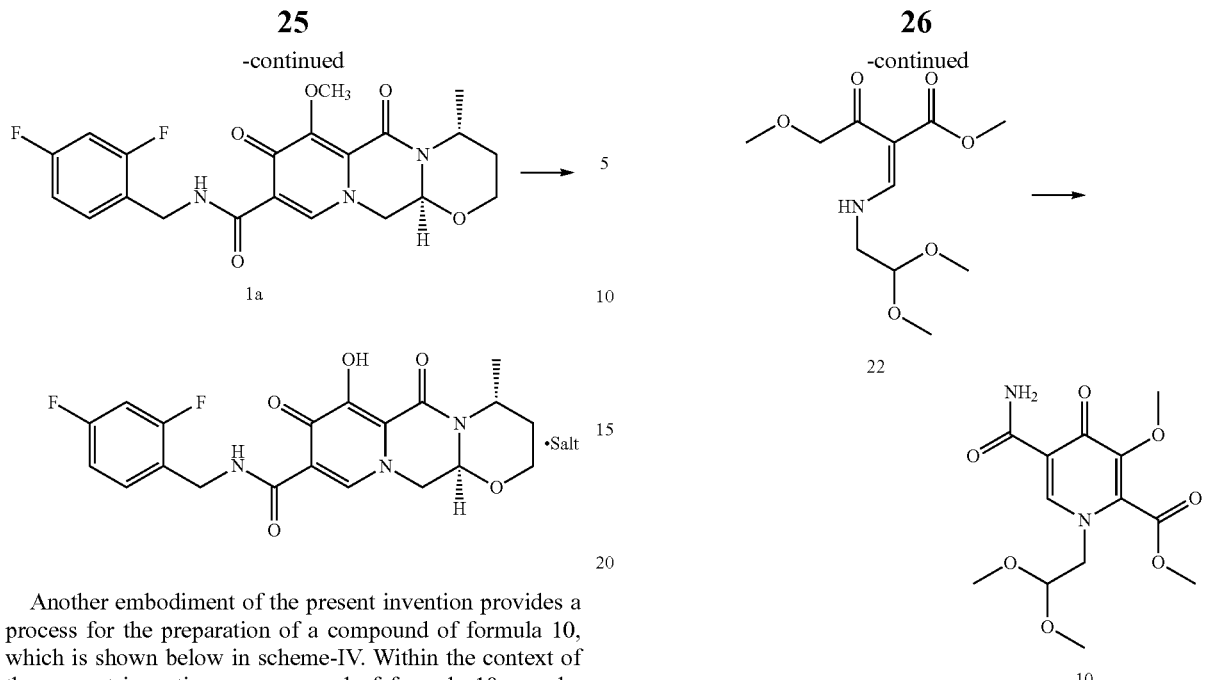

Another embodiment of the present invention provides a process for the preparation of a compound of formula 10, which is shown below in scheme-IV. Within the context of the present invention, a compound of formula 10 may be used as an intermediate for the preparation of dolutegravir or a pharmaceutically acceptable salt thereof.

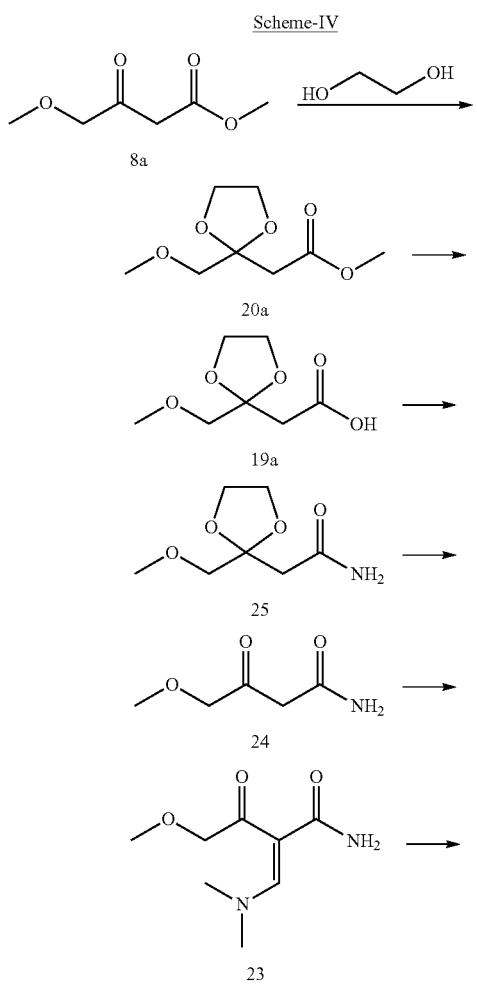

With all of the reactions disclosed above, one of skill in the art will recognize that the reaction conditions (e.g., reaction time or temperature) may be adjust to achieve appropriate yield without undertaking undue experimentation and without departing from the scope of the present invention.

With all of the reactions disclosed above, one of skill in the art will recognize that the reaction conditions (e.g., reaction time or temperature) may be adjusted to achieve appropriate yield without undertaking undue experimentation and without departing from the scope of the present invention.

The present invention provides methods for the preparation of dolutegravir. Conversion of dolutegravir to any pharmaceutically acceptable salt of dolutegravir, as well as to any theoretically possible tautomer, geometrical isomer, optically active compound, or racemate thereof is also within the scope of the present invention.

The dolutegravir and pharmaceutically acceptable salts as synthesized by the methods disclosed herein may be useful in the treatment of individuals infected with HIV, as dolutegravir has been demonstrated to be an effective HIV integrase inhibitor. Dolutegravir may be used singly or in combination with other anti-retroviral agents, such as abacavir, lamivudine, efavirenz, nevirapine, fosamprenavir, ritonavir, rifampin, tipranavir, or mixtures thereof.

The dolutegravir and pharmaceutically acceptable salts thereof may be formulated as an oral dosage form, for example a tablet or a capsule. The tablet may include excipients, for example, d-mannitol, microcrystalline cellulose, povidone K29/32, sodium starch glycolate, sodium stearyl fumarate, and mixtures thereof. The tablet may, in some embodiments, be coated with a film that includes additional excipients, artificial flavorings, artificial colorings, and mixtures thereof. For example, the coating may contain iron oxide yellow, macrogol/PEG, polyvinyl alcohol part-hydrolyzed, talc, titanium dioxide, or mixtures thereof.

In view of the above description and the examples below, one of ordinary skill in the art will be able to practice the invention as claimed without undue experimentation. The foregoing will be better understood with reference to the following examples that detail certain procedures for the preparation of molecules, compositions, and formulations according to the present invention. All references made to these examples for the purpose of illustration. The following examples should not be considered exhaustive, but merely illustrative of only a few of the many aspects and embodiments contemplated by the present invention.

Example 1: Preparation of 1-allyl-5-methoxy-6-(methoxycarbonyl)-4-oxo-1,4-dihydropyridine-3-carboxylic Acid (Formula 4a) by Indirect Conversion of a Compound of Formula 5b to a Compound of Formula 4a N,N-Dimethyl-1,1-bis(methyloxy)methanamine (196 g) was added to methyl-4-methoxy acetoacetate (formula 8a, 200 g) at 0-5° C. The temperature of the reaction mass was raised to 25-35° C. and stirred at the same temperature until complete consumption of starting material. The reaction mass was then diluted with methanol and cooled to 15-20° C. Allylamine (86 g) was added and stirring was continued at 25-35° C. until completion of reaction, as monitored by TLC. (NMR data of compound 6a: $^1$H NMR (CDCl$_3$): δ 3.61 (s, 3H), 4.40 (s, 2H), 3.29 (s, 3H), 8.02 (d, 1H, J=14.1 Hz), 4.05 (t, 2H, J=5.7 Hz), 5.87-6.00 (m, 1H), 5.16-5.22 (m, 2H), 10.80-10.84 (broad, 1H)) Thereafter, the solution was concentrated under reduced pressure and then diluted with methanol (700 mL). Dimethyl oxalate (404 g) was then added and the solution was warmed to 40-45° C. Next, a sodium methoxide solution (530 g of sodium methoxide dissolved in 1.4 L of methanol) was added and the solution was stirred until complete consumption of the starting material, as monitored by TLC. The reaction mass was poured into a mixture of water (3.5 L) and methylene dichloride (2.4 L). The pH adjusted to 4-5 using acetic acid and the solution was filtered. The organic layer was separated and concentrated to yield a crude residue of dimethyl 1-allyl-3-methoxy-4-oxo-1,4-dihydropyridine-2,5-dicarboxylate (NMR data of compound 5b: $^1$H NMR (CDCl$_3$): δ 8.39 (s, 1H), 4.63 (d, 2H, J=5.7 Hz), 5.86-5.99 (m, 1H), 5.15-5.21 (dd, 1H, J=17.1 Hz, 1.2 Hz), 5.26-5.30 (dd, 1H, J=10.2 Hz, 0.9 Hz), 3.77 (s, 3H), 3.74 (s, 3H), 3.88 (s, 3H)) Boric acid (85 g) was added in portions to acetic anhydride (560 g) and heated to 70° C. The boroacetate solution was heated further to 90° C. and maintained at that temperature for an hour. The crude residue of dimethyl 1-allyl-3-methoxy-4-oxo-1,4-dihydropyridine-2,5-dicarboxylate (formula 5b) diluted in acetic acid (440 mL) was then added to the boroacetate solution at 70-75° C. and stirring was maintained until complete conversion of starting material. The reaction mass was cooled to 2-5° C., water was added, and the solution was filtered to yield formula 5c (NMR data of compound of formula 5c: $^1$H NMR (CDCl$_3$): δ 9.22 (s, 1H), 5.10 (d, 2H, J=6.3 Hz), 6.00-6.13 (m, 1H), 5.33-5.43 (m, 2H), 3.84 (s, 3H), 4.00 (s, 3H), 1.92 (s, 6H)). Formula 5c was then hydrolyzed with methanolic HCl (150 mL) at 25-35° C. to give 1-allyl-5-methoxy-6-(methoxycarbonyl)-4-oxo-1,4-dihydropyridine-3-carboxylic acid as white solid (formula 4a, 239 g, $^1$H NMR (DMSO-d6): δ 8.75 (s, 1H), 4.83 (d, 2H, J=5.7 Hz), 5.89-6.02 (m, 1H), 5.22-5.28 (dd, 1H, J=17.1, 0.9 Hz), 5.30-5.34 (dd, 1H, J=10.2, 0.9 Hz), 3.89 (s, 3H), 3.93 (s, 3H), 15.28 (s, 1H)).

Example 2: Preparation of 1-allyl-5-methoxy-6-(methoxycarbonyl)-4-oxo-1,4-dihydropyridine-3-carboxylic Acid (Formula 4a) by Direct Conversion of a Compound of Formula 5b to a Compound of Formula 4a Methyl-4-methoxy acetoacetate (formula 8a, 20 g) was stirred with N,N-dimethyl-1,1-bis(methyloxy)methanamine (18 g) at 0-5° C. The progress of the reaction was monitored by TLC. After completion of reaction, methanol (40 mL) and allyamine (9 g) were added and the reaction was stirred until complete consumption of the starting material. The solution was concentrated and the residue was diluted with methanol (80 mL). Dimethyl oxalate (40 g) was then added and the reaction mass was heated to 40-45° C. A solution of sodium methoxide (16.27 g) in methanol (40 mL) was added and the reaction proceeded until complete consumption of the starting material. After completion of the reaction, the reaction mass was concentrated under reduced pressure and a mixture of water (100 mL) and methylene dichloride (200 mL) was added. The pH of the reaction mass was adjusted to 4-5 using acetic acid and the solution was filtered. The organic layer was separated, washed with brine solution (5 volumes), and concentrated to yield a crude residue of dimethyl 1-allyl-3-methoxy-4-oxo-1,4-dihydropyridine-2,5-dicarboxylate (formula 5b). The residue was dissolved in methanol (100 mL) and lithium hydroxide monohydrate (8.8 g) was added lot wise. The reaction was checked for reaction completion after 2 hours. After reaction completion, 3N HCl was added (78 mL) and stirred at 0-5° C. to obtain a solid, which was filtered and washed with water to give 1-allyl-5-methoxy-6-(methoxycarbonyl)-4-oxo-1,4-dihydropyridine-3-carboxylic acid (formula 4a, 12.5 g).

Example 3: Preparation of methyl 1-allyl-5-(2,4-difluorobenzylcarbamoyl)-3-methoxy-4-oxo-1,4-dihydropyridine-2-carboxylate (Formula 3a)

N-methyl morpholine (9.6 g) was added to a suspension of 1-allyl-5-methoxy-6-(methoxycarbonyl)-4-oxo-1,4-dihydropyridine-3-carboxylic acid (formula 4a, 23 g) in methylene dichloride (138 mL) and the solution was cooled to −10 to −15° C. A solution of isobutyl chloroformate (11.8 g) in methylene dichloride (46 mL) was added to the reaction mass slowly over 20-30 minutes and stirred at −10 to −15° C. for 1 hour. Thereafter, a solution of 2,4-difluorobenzylamine (12.32 g) in methylene dichloride (23 mL) was added at −10 to −15° C. and maintained at the same temperature for 2 hours after which the temperature of the reaction mass was raised to 25-35° C. to complete the reaction. The reaction mass was then washed with 5% (w/v) aqueous potassium carbonate solution (138 mL) twice, 10% (w/v) aqueous NaCl solution (92 mL), 5% (w/v) aqueous citric acid solution (138 mL), and finally with 5% (w/v) aqueous NaCl solution (92 mL). The organic layer was dried over anhydrous sodium sulfate (3 g) and concentrated under reduced pressure. The residue was further treated with methanol under reflux and cooled to obtain formula 3a (30 g).

Example 4: Preparation of methyl 5-(2,4-difluorobenzylcarbamoyl)-3-methoxy-4-oxo-1-(2-oxoethyl)-1,4-dihydropyridine-2-carboxylate (Formula 2a)

Methyl 1-allyl-5-(2,4-difluorobenzylcarbamoyl)-3-methoxy-4-oxo-1,4-dihydro pyridine-2-carboxylate (formula 3a, 5 g) was added into a tetrahydrofuran-water mixture (3:1) (135 mL) and the solution was stirred. An osmium tetroxide solution (2.5% in 3.2 mL tert-butanol) and sodium metaperiodate (10.9 g) were added. The reaction mass was stirred at room temperature until complete consumption of starting material. After completion, water (50 mL) was added followed by extraction with ethyl acetate (100 mL). The organic layer was washed with water, 5% aqueous sodium hydrogen sulfite solution, and an aqueous saturated sodium chloride solution, and then dried over anhydrous sodium sulfate. The solvent was distilled off under reduced pressure, and the residue was washed with diisopropyl ether to obtain methyl 5-(2,4-difluorobenzylcarbamoyl)-3-methoxy-4-oxo-1-(2-oxoethyl)-1,4-dihydropyridine-2-carboxylate (formula 2a, 3.2 g).

Example 5: Preparation of methyl 5-(2,4-difluorobenzylcarbamoyl)-3-methoxy-4-oxo-1-(2-oxoethyl)-1,4-dihydropyridine-2-carboxylate (Formula 2a)

A mixture of methyl 1-allyl-5-(2,4-difluorobenzylcarbamoyl)-3-methoxy-4-oxo-1,4-dihydropyridine-2-carboxylate (formula 3a, 5 g) and acetonitrile (15 mL) was stirred with ruthenium chloride monohydrate (92 mg). Potassium peroxymonosulfate (5.85 g) was added in one lot and the solution was stirred at room temperature until complete conversion of the starting material. After aqueous work up, extraction with methylene dichloride followed by washing with an aqueous saturated sodium chloride solution, the organic layer was dried over anhydrous sodium sulfate. The solvent was removed from the organic layer by distillation under reduced pressure and passed through silica gel column chromatography to yield the formula 2a (850 mg).

Example 6: Preparation of methyl 5-(2,4-difluorobenzylcarbamoyl)-3-methoxy-4-oxo-1-(2-oxoethyl)-1,4-dihydropyridine-2-carboxylate (Formula 2a)

Methyl 1-allyl-5-(2,4-difluorobenzylcarbamoyl)-3-methoxy-4-oxo-1,4-dihydro pyridine-2-carboxylate (formula 3a, 25 g) was dissolved in THF (500 mL). The solution was cooled to −65° C. and ozone gas was passed through the solution at −65 to −70° C., until ozonolysis was completed. The solution was purged with nitrogen to remove traces of dissolved ozone. Dimethyl sulfide (6 g) was added to the reaction mass. The solution was warmed to 25-35° C. slowly and maintained at the same temperature for 12 hours. Water (625 mL) and ethyl acetate (250 mL) were added to the reaction mass and the organic layer was separated. The organic layer was washed with 10% sodium chloride solution. Hexane (750 mL) was added to the organic layer, which was then stirred at 25-35° C., filtered, and dried to give methyl 5-(2,4-difluorobenzylcarbamoyl)-3-methoxy-4-oxo-1-(2-oxoethyl)-1,4-dihydropyridine-2-carboxylate (formula 2a, 18 g).

Example 7: Preparation of methyl 5-(2,4-difluorobenzylcarbamoyl)-3-methoxy-4-oxo-1-(2-oxoethyl)-1,4-dihydropyridine-2-carboxylate (Formula 2a)

Methyl 1-allyl-5-(2,4-difluorobenzylcarbamoyl)-3-methoxy-4-oxo-1,4-dihydro pyridine-2-carboxylate (formula 3a, 38.26 mmol) was charged with acetic acid. The solution was cooled to −25° C. and ozonized oxygen (38.26 mmol) was passed through the reaction mixture for 60 minutes at which time the reaction was checked for completion. Nitrogen was purged through the solution to remove traces of dissolved ozone. The contents of the flask were poured into a flask containing zinc dust (2.62 g) and left under stirring for 3 hours. Water (75 mL) and ethyl acetate (150 mL) were added and the organic layer was separated, washed with aqueous saturated sodium chloride solution, and dried over anhydrous sodium sulfate. The solvent was removed from the organic layer by distillation under reduced pressure and passed through silica gel column chromatography to yield formula 2a (95% purity).

Example 8: Preparation of (4R,12aS)—N-(2,4-difluorobenzyl)-7-methyoxy-4-methyl-6,8-dioxo-3,4,6,8,12,12a-hexahydro-2H-pyrido[1',2':4,5]pyrazino[2,1-b][1,3] oxazine-9-carboximide (Formula 1a)

Methyl 1-allyl-5-(2,4-difluorobenzylcarbamoyl)-3-methoxy-4-oxo-1,4-dihydro pyridine-2-carboxylate (formula 3a, 100 g) in 5% aqueous tetrahydrofuran (1500 mL) was added to a three-neck round bottom flask. Ozone gas was then passed through the reaction mixture for 4 hours while maintaining the temperature at −20 to −10° C. The reaction mixture was then purged with nitrogen gas, the temperature was raised to 25-35° C., and water (1000 mL) and ethylacetate (1000 mL) were added. The reaction mixture was stirred and the organic layer was separated and washed with 5% sodium dithionite solution (300 mL). The organic layer was then washed with 10% NaCl solution (500 mL). The solvent was distilled off under reduced pressure residual mass obtained to this stripping with acetonitrile (100 mL). Residual mass was added into acetonitrile (400 mL) and acetic acid (30.61 g), the temperature was raised to 70° C., and a solution of 3R-aminobutanol (27.24 g) and acetonitrile (100 mL) was added. The solution was further stirred for 12 hours. The reaction mixture was cooled to 25-35° C., water (500 mL) was added, and the pH was adjusted to 8-9 using 10% NaOH solution (175 mL). The product was then extracted by adding methylene dichloride (500 mL) and the organic layer was separated out. Methylene dichloride (300 mL) was added to the aqueous layer and the layers were separated. The combined organic layers were washed with water (400 mL). The solvent was completely distilled off under reduced pressure to obtained a thick residue which was stripped with isopropyl alcohol (100 mL) and recrystallized from isopropyl alcohol (200 mL) and n-heptane (100 mL) to obtain (4R,12aS)—N-(2,4-difluorobenzyl)-7-methyoxy-4-methyl-6,8-dioxo-3,4,6,8,12,12a-hexahydro-2H-pyrido[1',2':4,5]pyrazino[2,1-b][1,3]oxazine-9-carboximide (formula 1a, 66 g).

Example 9: Preparation of Dolutegravir

Anhydrous $MgBr_2$ (202.1 g) was added to a solution of (4R,12aS)—N-(2,4-difluorobenzyl)-7-methyoxy-4-methyl-6,8-dioxo-3,4,6,8,12,12a-hexahydro-2H-pyrido[1',2': 4,5]pyrazino[2,1-b][1,3]oxazine-9-carboximide (formula 1a, 120 g) in acetonitrile (480 mL). The reaction mixture was heated to 50-52° C. for 8 hours. The reaction mixture was then cooled to 25-35° C. and the acetonitrile layer was siphoned out. Methylene dichloride (1800 mL) and dilute HCl solution (240 mL HCl+1056 mL water) was added to the residual mass, and the solution was stirred. The organic layer was separated off, washed with water, and the solvent was distilled off under reduced pressure. The residue was crystallized from methanol to obtain dolutegravir (67 g).

Example 10: Preparation of (E)-methyl 2-((2,2-dimethoxyethylamino)methylene)-4-methoxy-3-oxobutanoate (Formula 14)

Methyl-4-methoxy acetoacetate (formula 8a, 200 g) was cooled to 0° C. 1,1-dimethoxy-N,N-dimethyl methanamine (195 g) was added and the solution was stirred for 12 hours at 25-35° C. after which the reaction mass was diluted with methanol and cooled to 20° C. Aminoacetaldehyde dimethyl acetal (158 g) was added slowly and the temperature was raised to 25-35° C. and maintained until the starting material was consumed, as measured by TLC. The solvent was concentrated and the residue was partitioned between water (500 mL) and methylene dichloride (1000 mL). The organic layer was separated and the solvent was removed by distillation. The residue was stirred with hexanes (600 mL) and filtered to obtain a yellow solid (E)-methyl 2-((2,2-dimethoxyethylamino)methylene)-4-methoxy-3-oxobutanoate (formula 14, 305 g).

Example 11: Preparation of dimethyl 1-(2,2-dimethoxyethyl)-3-methoxy-4-oxo-1,4-dihydropyridine-2,5-dicarboxylate (Formula 13)

A 60% dispersion of sodium hydride in mineral oil (1.9 g) in THF (100 mL) was charged in clean dry RBF and stirred under nitrogen atmosphere. To this suspension, a solution of dimethyl oxalate (10 g) in THF (100 mL) was added under inert atmosphere and heated to reflux. A solution of (E)-methyl 2-((2,2-dimethoxyethylamino)methylene)-4-methoxy-3-oxobutanoate (formula 14, 10 g) in THF (50 mL) was added at reflux and maintained for 90 minutes. The reaction mixture was cooled to 25° C., hexanes (100 mL) was added, and the solution was stirred and filtered. Water (50 mL) was added slowly to the filtrate and the aqueous and organic layers were separated. The aqueous layer was extracted with methylene dichloride. The solvent from the combined organic layers was concentrated under vacuum to give a crude residue which was purified by silica gel chromatography using 5% ethyl acetate in hexane to give pure dimethyl 1-(2,2-dimethoxyethyl)-3-methoxy-4-oxo-1,4-dihydropyridine-2,5-dicarboxylate (formula 13, 2.5 g).

Example 12: Preparation of dimethyl 1-(2,2-dimethoxyethyl)-3-methoxy-4-oxo-1,4-dihydropyridine-2,5-dicarboxylate Boron Complex (Formula 12)

Acetic anhydride (186 g) was heated to 70° C. Boric acid (22 g) was added lot-wise and the reaction was allowed to proceed for 10 minutes after which the temperature was raised to 90° C. and maintained there for one hour. The reaction mass was cooled to 50° C. A solution of dimethyl 1-(2,2-dimethoxyethyl)-3-methoxy-4-oxo-1,4-dihydropyridine-2,5-dicarboxylate (formula 13, 100 g) in toluene (200 mL) was added and the solution was stirred at the same temperature for one hour. The reaction mass was cooled to 25-35° C. and water (1000 mL) was added. The solution was stirred and filtered to give dimethyl 1-(2,2-dimethoxyethyl)-3-methoxy-4-oxo-1,4-dihydropyridine-2,5-dicarboxylate boron complex (formula 12, 91 g).

Example 13: Preparation of 1-(2,2-dimethoxyethyl)-5-methoxy-6-methoxy carbonyl-4-oxo-1,4-dihydropyridine-3-carboxylic Acid (Formula 11)

A solution of dimethyl 1-(2,2-dimethoxyethyl)-3-methoxy-4-oxo-1,4-dihydropyridine-2,5-dicarboxylate boron complex (formula 12, 5 g) in methanol (75 mL) was cooled to 10° C. Aqueous hydrochloric acid (2 g) was added and the solution was maintained at 25-35° C. for 2 hours. Water (40 mL) was added to the reaction mixture and cooled to 10° C. and the solution was stirred and filtered to give 1-(2,2-dimethoxyethyl)-5-methoxy-6-methoxycarbonyl-4-oxo-1,4-dihydropyridine-3-carboxylic acid (formula 11, 1.8 g).

Example 14: Preparation of methyl 5-carbamoyl-1-(2,2-dimethoxyethyl)-3-methoxy-4-oxo-1,4-dihydropyridine-2-carboxylate (Formula 10)

A mixture of 1-(2,2-dimethoxyethyl)-5-methoxy-6-(methoxycarbonyl)-4-oxo-1,4-dihydropyridine-3-carboxylic acid (formula 11, 100 g), 1-(3-dimethylaminopropyl)-3-ethylcarbodiimide HCl (85 g), hydroxyl benzotriazole monohydrate (58.3 g), and ammonium chloride (34 g) in THF (800 mL) was stirred at 25-30° C. followed by the addition of diisopropyl ethylamine (122.9 g). The reaction mass was stirred until complete consumption of starting material. The solvent was evaporated and 20% aqueous potassium carbonate (300 mL) and ethyl acetate (500 mL) were added. The solution was stirred and the organic layer was separated out and washed with saturated brine solution. The organic layer was distilled under reduced pressure to result in a residue. The residue was then stirred with diisopropyl ether and filtered to yield methyl 5-carbamoyl-1-(2,2-dimethoxyethyl)-3-methoxy-4-oxo-1,4-dihydropyridine-2-carboxylate (formula 10, 74 g, 74% yield).

Example 15: Preparation of (4R,12aS)-7-methoxy-4-methyl-6,8-dioxo-3,4,6,8,12,12a-hexahydro-2H-[1,3]oxazino[3,2-d]pyrido[1,2-a]pyrazine-9-carboxamide (Formula 9)

Water (10 mL), acetic acid (90 mL), and methane sulfonic acid (0.62 g) were added to a solution of methyl 5-carbamoyl-1-(2,2-dimethoxyethyl)-3-methoxy-4-oxo-1,4-dihydropyridine-2-carboxylate (formula 10, 10 g) in acetonitrile (100 mL). The solution was stirred under reflux until complete consumption of the starting material, which was monitored by TLC. The reaction mass was cooled to 70° C., (R)-3-aminobutanol (4.25 g) diluted in acetonitrile was added, and the solution was stirred at the same temperature until complete consumption of starting material. The reaction mass was cooled to 30° C., water (20 mL) was added, and the pH as adjusted to 7.5 using 10% aqueous sodium hydroxide solution. Methylene dichloride was added and the organic layer was separated, washed with saturated aqueous brine solution, and distilled under reduced pressure to give a residue. The residue was then stirred with a mixture of methylene dichloride (10 mL) and diisopropyl ether (50 mL) to yield the cyclized amide (4R,12aS)-7-methoxy-4-methyl-6,8-dioxo-3,4,6,8,12,12a-hexahydro-2H-[1,3]oxazino[3,2-d]pyrido[1,2-a]pyrazine-9-carboxamide (formula 9).

Example 16: Preparation of (4R,12aS)—N-(2,4-difluorobenzyl)-7-methyoxy-4-methyl-6,8-dioxo-3,4,6,8,12,12a-hexahydro-2H-pyrido[1',2':4,5]pyrazino[2,1-b][1,3]oxazine-9-carboximide (Formula 1a)

Triethylsilane (3.4 g) was added to a mixture of (4R, 12aS)-7-methoxy-4-methyl-6,8-dioxo-3,4,6,8,12,12a-hexahydro-2H-[1,3]oxazino [3,2-d]pyrido[1,2-a] pyrazine-9-carboxamide (formula 9, 3 g) and 2,4-diflurobenzaldehyde (4.2 g) in toluene (33 mL). Trifluoroacetic acid (3.25 g) was then added. The reaction mixture was heated to reflux and maintained until complete conversion of the starting material, after which the mass was cooled to 30° C. Water (9 mL) was added and the pH was adjusted to 7-7.5 using 5% aqueous sodium bicarbonate solution. The aqueous layer was extracted with ethyl acetate (2×15 mL), washed with saturated aqueous sodium chloride solution, and distilled under reduced pressure to obtain a residue which was heated with isopropyl alcohol (6 mL) and n-heptane (25 mL) to 60° C. and cooled to give (4R,12aS)—N-(2,4-difluorobenzyl)-7-methyloxy-4-methyl-6,8-dioxo-3,4,6,8,12,12a-hexahydro-2H-pyrido[1',2':4,5]pyrazino[2,1-b][1,3]oxazine-9-carboximide (formula 1a, 600 mg).

Example 17: Preparation of Dolutegravir

Anhydrous $MgBr_2$ (168.5 g) was added to a solution of (4R,12aS)—N-(2,4-difluorobenzyl)-7-methyloxy-4-methyl-6,8-dioxo-3,4,6,8,12,12a-hexahydro-2H-pyrido[1',2':4,5]pyrazino[2,1-b][1,3]oxazine-9-carboximide (formula 1a, 100 g) in acetonitrile (400 mL). The reaction mixture was heated to 50-52° C. for 8 hours. The reaction mixture was then cooled to 25-35° C. and the acetonitrile layer was siphoned out. Methylene dichloride (1500 mL) and dilute hydrochloride solution (220 mL HCl+880 mL water) was added to the residual mass and the solution was stirred. The organic layer was separated, washed with water, and the solvent was distilled off under reduced pressure. The residue was crystallized from methanol to obtain dolutegravir (67 g).

Example 18: Preparation of Dolutegravir Sodium

Dolutegravir (50 g) was dissolved in n-butanol (2500 mL) and methanol (750 mL). The reaction mass was filtered through filter paper and a methanolic sodium hydroxide solution (5.25 g NaOH in 500 mL methanol) was added to the filtrate. The suspension was stirred for 16 hours and filtered. The solid was then dried at 100° C., milled and further dried at 130° C. to obtain dolutegravir sodium (52 g).

Example 19: Preparation of Dolutegravir Sodium

Dolutegravir (50 g) was dissolved in methylene dichloride (350 mL) and to it was charged n-butanol (350 mL). The reaction mass was filtered through filter paper and a butanolic sodium methoxide solution (7 g sodium methoxide in 150 mL n-butanol) was added to the filtrate. The suspension was stirred for 16 hours and filtered. The solid was then dried at 100° C., milled and further dried at 130° C. to obtain dolutegravir sodium (50 g).

What is claimed is:

1. A process for the preparation of dolutegravir, comprising the steps of:

a) reacting a compound of formula 8 with 1,1-dimethoxy-N,N-dimethyl methanamine to obtain a compound of formula 7;

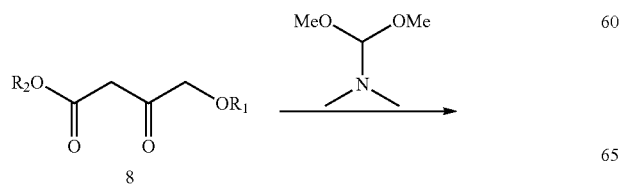

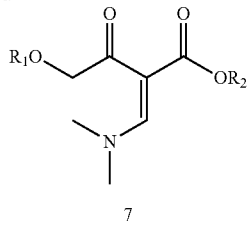

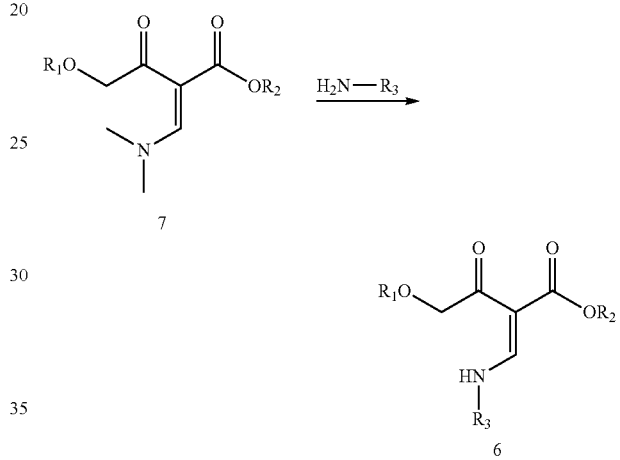

b) treating the compound of formula 7 with an alkenyl amine of the formula $H_2N-R_3$ in the presence of a solvent to obtain a compound of formula 6, wherein the solvent is selected from the group consisting of alcohol solvent, ester solvent, ether solvent, aromatic hydrocarbon solvent, and mixtures thereof;

c) cyclizing the compound of formula 6 with dimethyl oxalate in the presence of a base and a solvent to obtain a compound of formula 5, wherein the base is selected from the group consisting of an alkali metal hydroxide, an alkali metal hydride, an alkali metal alkoxide, and mixtures thereof, and the solvent is an alcohol;

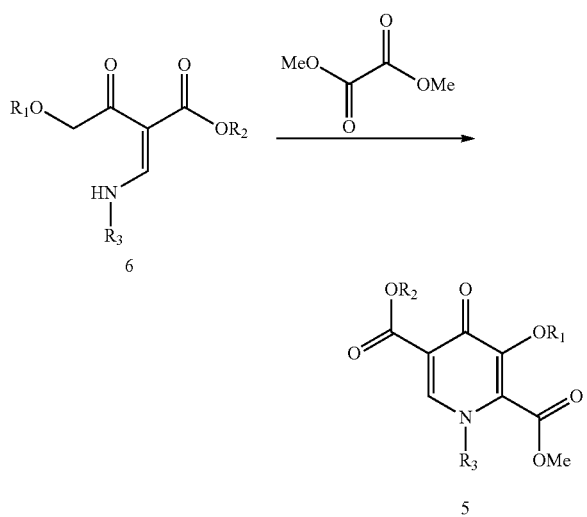

d) converting the compound of formula 5 to a compound of formula 5a and then converting the compound of formula 5a to the compound of formula 4,
wherein converting the compound of formula 5 to the compound of formula 5a comprises mixing boric acid with acetic anhydride which is then reacted with the compound of formula 5 to result in the compound of formula 5a, and
wherein converting the compound of formula 5a to the compound of formula 4 is performed in the presence of a base or an acid and a solvent, wherein the base is an alkali metal hydroxide base;

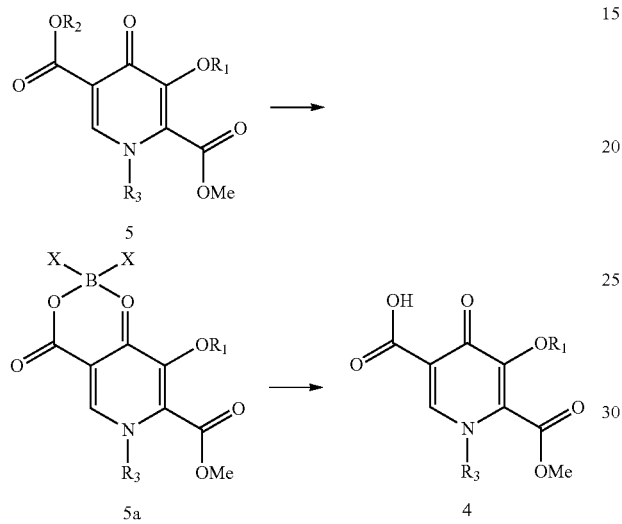

e) condensing the compound of formula 4 with 2,4-difluorobenzylamine in the presence of a base and a coupling agent in a solvent to obtain a compound of formula 3, wherein the base is selected from the group consisting of N-methylmorpholine (NMM), diisopropylethylamine, trimethylamine, N,N'-dimethylpiperazine, N-methylpiperidine, pyridine, and mixtures thereof;

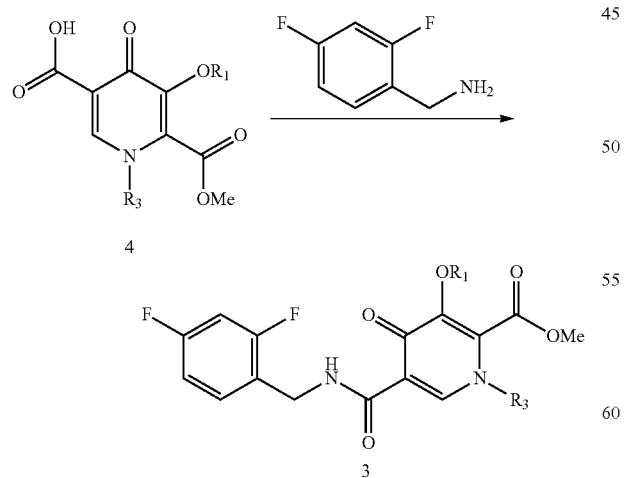

f) oxidizing the compound of formula 3 by reacting the compound of formula 3 with an oxidizing agent to obtain a compound of formula 2, wherein the oxidizing agent is selected from the group consisting of ozone, ozonized oxygen, periodic acid, osmium tetroxide-periodate, ruthenium trichloride-periodate, sodium metaperiodate, sodium orthoperiodate, ruthenium trichloride/potassium peroxymonosulfate, bis(acetonitrile)dichloropalladium (II), bis(benzonitrile)palladium (II) chloride, osmium tetroxide, sodium metaperiodate, ruthenium trichloride/potassium peroxymonosulfate, and mixtures thereof;

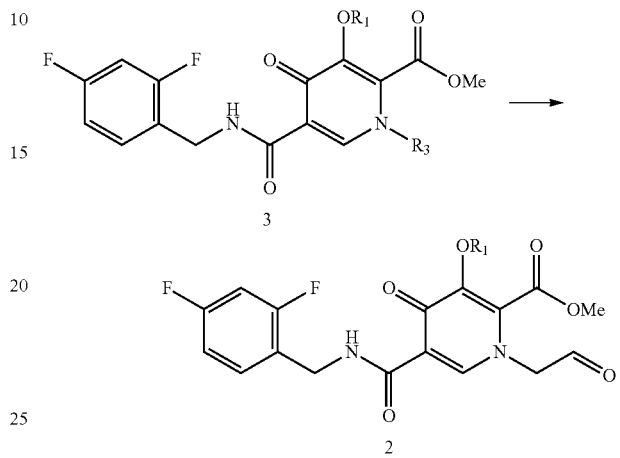

g) reacting the compound of formula 2 with (R)-3-aminobutanol in the presence of an acid and a solvent to obtain a compound of formula 1, wherein the acid is selected from the group consisting of acetic acid, methane sulfonic acid, p-toluenesulfonic acid, and mixtures thereof; and

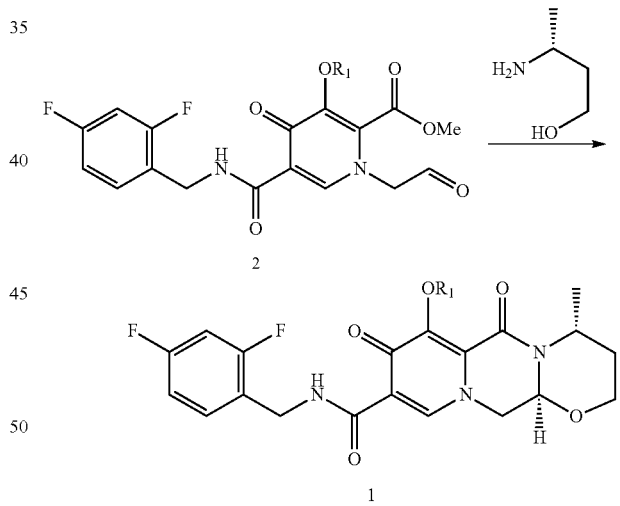

h) converting the compound of formula 1 in the presence of a metal bromide to dolutegravir;

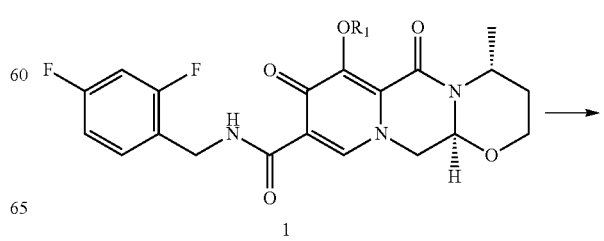

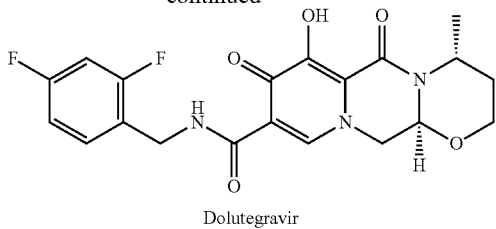

Dolutegravir wherein $R_1$ and $R_2$ are independently a $C_1$-$C_6$ alkyl, a $C_6$-$C_{10}$ aryl, or a $C_6$-$C_{10}$ aralkyl, and $R_4$ the alkenyl amine of the formula $H_2N-R_3$ is allyamine, and X is O-Acyl.

2. The process according to claim 1, wherein, in step b), the solvent is methanol.

3. The process according to claim 1, wherein the solvent used in converting the compound of formula 5a to the compound of formula 4 is selected from the group consisting of alcohol solvent, ester solvent, aromatic hydrocarbon solvent, ketone solvent, chlorinated hydrocarbon solvent, and mixtures thereof.

4. The process according to claim 1, wherein the acid used in converting the compound of formula 5a to the compound of formula 4 is selected from the group consisting of hydrochloric acid, hydrobromic acid, sulfuric acid, formic acid, acetic acid, trifluoroacetic acid, p-toluene sulfonic acid, and mixtures thereof.

5. The process according to claim 1, wherein the alkali metal hydroxide base used in converting the compound of formula 5a to the compound of formula 4 is selected from the group consisting of lithium hydroxide, sodium hydroxide, potassium hydroxide, cesium hydroxide, and mixtures thereof.

6. The process according to claim 1, wherein the solvent used in converting the compound of formula 5a to the compound of formula 4 is methanol and the acid is hydrochloric acid in methanol.

7. The process according to claim 1, wherein the base used in condensing step e) is N-methylmorpholine.

8. The process according to claim 1, wherein the coupling agent used in condensing step e) is selected from the group consisting of isobutyl chloroformate, carbonyldiimidazole (CDI), pivaloyl chloride, o-benzotriazole-1-yl-1,1,3,3,-tetramethyluronium tetrafluoroborate (TBTU), 2-(1H-benzotriazole-1-yl)-1,1,3,3-tetramethyluronium (HBTU), benzotriazole-1-yl-oxy-tris(dimethylamino)phosphonium (BOP), benzotriazole-1-yl-oxy-tris(pyrrolidino) phosphonium (PyBOP), bromo-tris-pyrrolidino-phosphoniumhexafluorophosphate (PyBrOP), tris(pyrrolidino)phosphonium hexafluorophosphate (pyCOP), ethyl cyanoglyoxylate-2-oxime, o-(6-chloro-1-hydoxybenzotriazol-1-yl)-1,1,3,3-tetramethyluronium tetrafluoroborate (TCTU), 2-(1H-7-azabenzotriazol-1-yl)-1,1,3,3-tetramethyl uranium hexafluorophosphate (HATU), 1-cyano-2-ethoxy-2-oxoethydenminooxy)dimethylamino-morpholino-carbenium hexafluorophosphate (COMU), and mixtures thereof.

9. The method according to claim 8, wherein the coupling agent is isobutyl chloroformate.

10. The process according to claim 1, wherein the condensing step e) is carried out optionally in the presence of an additive selected from the group consisting of hydroxyl benzotriazole (HOBt), 1-hydroxy-7-azabenzotriazole (HOAt), 6-chloro-1-hydroxy-1H-benzotriazole (Cl-HOBt), hydroxypyridines (HOPy), imidazole or its salts, 1,8-diazabicyclo[5.4.0]undex-7-en (DBU), dimethylaminopyridine (DMAP), and mixtures thereof.

11. The process of claim 1, further comprising converting dolutegravir to a pharmaceutically acceptable salt of dolutegravir.

12. The process of claim 1, wherein $R_1$ and $R_2$ are methyl groups.

13. The process of claim 1, wherein, in step c), the base is sodium methoxide and the solvent is methanol.

14. The process of claim 1, wherein the oxidizing agent is selected from the group consisting of osmium tetroxide, sodium metaperiodate, ruthenium trichloride/potassium peroxymonosulfate, and mixtures thereof.

15. The process of claim 1, wherein the acid used in step g) is acetic acid.

16. The process of claim 1, wherein the oxidizing agent is ozone, ozonized oxygen, or mixtures thereof.

* * * * *